US011992326B2

(12) United States Patent
Ghaffari et al.

(10) Patent No.: US 11,992,326 B2
(45) Date of Patent: May 28, 2024

(54) METHOD AND SYSTEM FOR MEASURING PERSPIRATION

(71) Applicant: Medidata Solutions, Inc., New York, NY (US)

(72) Inventors: Roozbeh Ghaffari, Cambridge, MA (US); Gilbert Lee Huppert, Stoneham, MA (US); Brian Murphy, Medford, MA (US); Isaiah Kacyvenski, Weston, MA (US)

(73) Assignee: Medidata Solutions, Inc., New York, NY (US)

( * ) Notice: Subject to any disclaimer, the term of this patent is extended or adjusted under 35 U.S.C. 154(b) by 120 days.

(21) Appl. No.: 17/486,194

(22) Filed: Sep. 27, 2021

(65) Prior Publication Data
US 2022/0007998 A1  Jan. 13, 2022

Related U.S. Application Data

(62) Division of application No. 15/491,379, filed on Apr. 19, 2017, now Pat. No. 11,154,235.
(Continued)

(51) Int. Cl.
*A61B 5/00* (2006.01)
*A61B 5/145* (2006.01)

(52) U.S. Cl.
CPC ........ *A61B 5/4266* (2013.01); *A61B 5/14517* (2013.01); *A61B 5/6833* (2013.01);
(Continued)

(58) Field of Classification Search
CPC . A61B 5/4266; A61B 5/14517; A61B 5/6833; A61B 5/002; A61B 5/14532;
(Continued)

(56) References Cited

U.S. PATENT DOCUMENTS

| 3,207,694 A | 9/1965 | Gogek |
| 3,716,861 A | 2/1973 | Root |
(Continued)

FOREIGN PATENT DOCUMENTS

| CN | 101084038 A | 12/2007 |
| CN | 202068986 U | 12/2011 |
(Continued)

OTHER PUBLICATIONS

Carvalhal et al., "Electrochemical Detection in a Paper-Based Separation Device", Analytical Chemistry, vol. 82, No. 3, (1162-1165) (4 pages) (Jan. 7, 2010).
(Continued)

*Primary Examiner* — May A Abouelela
(74) *Attorney, Agent, or Firm* — Nixon Peabody LLP

(57) ABSTRACT

A perspiration sensing system includes a sensor patch and a smart device. The sensor patch includes one or more perspiration sensing portions. The one or more perspiration sensing portions include an inlet having a predefined size to receive perspiration from a predefined number of sweat glands and an outlet for reducing back pressure. At least one perspiration sensing portion includes a channel having a colorimetric sensing material that changes color when exposed to perspiration. At least one perspiration sensing portion includes a colorimetric assay in a substrate that changes color when exposed to biochemical components of perspiration. The system further includes a smart device having a camera that can take a picture of the sensor patch and determine the volume, rate of perspiration, and/or biochemical components of the perspiration from the one or more perspiration sensing portions.

24 Claims, 10 Drawing Sheets

Related U.S. Application Data

(60) Provisional application No. 62/324,723, filed on Apr. 19, 2016.

(52) U.S. Cl.
CPC ............ *A61B 5/002* (2013.01); *A61B 5/14532* (2013.01); *A61B 5/14539* (2013.01); *A61B 5/14546* (2013.01); *A61B 5/6824* (2013.01)

(58) Field of Classification Search
CPC ............ A61B 5/14539; A61B 5/14546; A61B 5/6824; A61B 2560/0223; A61B 2560/0238; A61B 2560/0271; A61B 2560/0247; A61B 5/00
See application file for complete search history.

(56) References Cited

U.S. PATENT DOCUMENTS

| | | | |
|---|---|---|---|
| 3,805,427 | A | 4/1974 | Epstein |
| 3,838,240 | A | 9/1974 | Schelhorn |
| 3,892,905 | A | 7/1975 | Albert |
| 4,136,162 | A | 1/1979 | Fuchs |
| 4,278,474 | A | 7/1981 | Blakeslee |
| 4,304,235 | A | 12/1981 | Kaufman |
| 4,416,288 | A | 11/1983 | Freeman |
| 4,658,153 | A | 4/1987 | Brosh |
| 4,766,670 | A | 8/1988 | Gazdik |
| 4,911,169 | A | 3/1990 | Ferrari |
| 4,968,137 | A | 11/1990 | Yount |
| 5,059,424 | A | 10/1991 | Cartmell |
| 5,064,576 | A | 11/1991 | Suto |
| 5,272,375 | A | 12/1993 | Belopolsky |
| 5,278,627 | A | 1/1994 | Aoyagi |
| 5,306,917 | A | 4/1994 | Black |
| 5,326,521 | A | 7/1994 | East |
| 5,331,966 | A | 7/1994 | Bennett |
| 5,360,987 | A | 11/1994 | Shibib |
| 5,413,592 | A | 5/1995 | Schroeppel |
| 5,471,982 | A | 5/1995 | Edwards |
| 5,454,270 | A | 10/1995 | Brown |
| 5,491,651 | A | 2/1996 | Janic |
| 5,567,975 | A | 10/1996 | Walsh |
| 5,580,794 | A | 12/1996 | Allen |
| 5,617,870 | A | 4/1997 | Hastings |
| 5,676,144 | A | 10/1997 | Schoendorfer |
| 5,811,790 | A | 9/1998 | Endo |
| 5,817,008 | A | 10/1998 | Rafert |
| 5,907,477 | A | 5/1999 | Tuttle |
| 6,063,046 | A | 5/2000 | Allum |
| 6,211,799 | B1 | 4/2001 | Post |
| 6,220,916 | B1 | 4/2001 | Bart |
| 6,265,090 | B1 | 7/2001 | Nishide |
| 6,270,872 | B1 | 8/2001 | Cline |
| 6,282,960 | B1 | 9/2001 | Samuels |
| 6,343,514 | B1 | 2/2002 | Smith |
| 6,387,052 | B1 | 5/2002 | Quinn |
| 6,403,397 | B1 | 6/2002 | Katz |
| 6,410,971 | B1 | 6/2002 | Otey |
| 6,421,016 | B1 | 7/2002 | Phillips |
| 6,450,026 | B1 | 9/2002 | Desarnaud |
| 6,455,931 | B1 | 9/2002 | Hamilton |
| 6,479,395 | B1 | 11/2002 | Smith |
| 6,567,158 | B1 | 5/2003 | Falcial |
| 6,626,940 | B2 | 9/2003 | Crowley |
| 6,628,987 | B1 | 9/2003 | Hill |
| 6,641,860 | B1 | 11/2003 | Kaiserman |
| 6,775,906 | B1 | 8/2004 | Silverbrook |
| 6,784,844 | B1 | 8/2004 | Boakes |
| 6,825,539 | B2 | 11/2004 | Tai |
| 6,965,160 | B2 | 11/2005 | Cobbley |
| 6,987,314 | B1 | 1/2006 | Yoshida |
| 7,259,030 | B2 | 8/2007 | Daniels |
| 7,265,298 | B2 | 9/2007 | Maghribi |
| 7,302,751 | B2 | 12/2007 | Hamburgen |
| 7,337,012 | B2 | 2/2008 | Maghribi |
| 7,487,587 | B2 | 2/2009 | Vanfleteren |
| 7,491,892 | B2 | 2/2009 | Wagner |
| 7,521,292 | B2 | 4/2009 | Rogers |
| 7,557,367 | B2 | 7/2009 | Rogers |
| 7,618,260 | B2 | 11/2009 | Daniel |
| 7,622,367 | B1 | 11/2009 | Nuzzo |
| 7,727,228 | B2 | 6/2010 | Abboud |
| 7,739,791 | B2 | 6/2010 | Brandenburg |
| 7,759,167 | B2 | 7/2010 | Vanfleteren |
| 7,815,095 | B2 | 10/2010 | Fujisawa |
| 7,960,246 | B2 | 6/2011 | Flamand |
| 7,982,296 | B2 | 7/2011 | Nuzzo |
| 8,097,926 | B2 | 1/2012 | De Graff |
| 8,198,621 | B2 | 6/2012 | Rogers |
| 8,207,473 | B2 | 6/2012 | Axisa |
| 8,217,381 | B2 | 7/2012 | Rogers |
| 8,332,053 | B1 | 12/2012 | Patterson |
| 8,372,726 | B2 | 2/2013 | De Graff |
| 8,389,862 | B2 | 3/2013 | Arora |
| 8,431,828 | B2 | 4/2013 | Vanfleteren |
| 8,440,546 | B2 | 5/2013 | Nuzzo |
| 8,536,667 | B2 | 9/2013 | De Graff |
| 8,552,299 | B2 | 10/2013 | Rogers |
| 8,609,471 | B2 | 12/2013 | Xu |
| 8,618,656 | B2 | 12/2013 | Oh |
| 8,664,699 | B2 | 3/2014 | Nuzzo |
| 8,679,888 | B2 | 3/2014 | Rogers |
| 8,729,524 | B2 | 5/2014 | Rogers |
| 8,754,396 | B2 | 6/2014 | Rogers |
| 8,865,489 | B2 | 10/2014 | Rogers |
| 8,886,334 | B2 | 11/2014 | Ghaffari |
| 8,905,772 | B2 | 12/2014 | Rogers |
| 9,012,784 | B2 | 4/2015 | Arora |
| 9,082,025 | B2 | 7/2015 | Fastert |
| 9,105,555 | B2 | 8/2015 | Rogers |
| 9,105,782 | B2 | 8/2015 | Rogers |
| 9,107,592 | B2 | 8/2015 | Litt |
| 9,119,533 | B2 | 9/2015 | Ghaffari |
| 9,123,614 | B2 | 9/2015 | Graff |
| 9,133,024 | B2 | 9/2015 | Phan |
| 9,159,635 | B2 | 10/2015 | Elolampi |
| 9,168,094 | B2 | 10/2015 | Lee |
| 9,171,794 | B2 | 10/2015 | Rafferty |
| 9,186,060 | B2 | 11/2015 | De Graff |
| 9,226,402 | B2 | 12/2015 | Hsu |
| 9,247,637 | B2 | 1/2016 | Hsu |
| 9,289,132 | B2 | 3/2016 | Ghaffari |
| 9,295,842 | B2 | 3/2016 | Ghaffari |
| 9,320,907 | B2 | 4/2016 | Bogie |
| 9,324,733 | B2 | 4/2016 | Rogers |
| 9,372,123 | B2 | 6/2016 | Li |
| 9,408,305 | B2 | 8/2016 | Hsu |
| 9,420,953 | B2 | 8/2016 | Litt |
| 9,450,043 | B2 | 9/2016 | Nuzzo |
| 9,515,025 | B2 | 12/2016 | Rogers |
| 9,516,758 | B2 | 12/2016 | Arora |
| 9,545,216 | B2 | 1/2017 | D'Angelo |
| 9,545,285 | B2 | 1/2017 | Ghaffari |
| 9,554,850 | B2 | 1/2017 | Lee |
| 9,579,040 | B2 | 2/2017 | Rafferty |
| 9,583,428 | B2 | 2/2017 | Rafferty |
| D781,270 | S | 3/2017 | Li |
| 9,622,680 | B2 | 4/2017 | Ghaffari |
| 9,629,586 | B2 | 4/2017 | Ghaffari |
| 9,647,171 | B2 | 5/2017 | Rogers |
| 9,655,560 | B2 | 5/2017 | Ghaffari |
| 9,662,069 | B2 | 5/2017 | De Graff |
| 9,702,839 | B2 | 7/2017 | Ghaffari |
| 9,704,908 | B2 | 7/2017 | De Graff |
| 9,706,647 | B2 | 7/2017 | Hsu |
| 9,723,122 | B2 | 8/2017 | Ghaffari |
| 9,723,711 | B2 | 8/2017 | Elolampi |
| 9,750,421 | B2 | 9/2017 | Ghaffari |
| 9,757,050 | B2 | 9/2017 | Ghaffari |
| 9,761,444 | B2 | 9/2017 | Nuzzo |
| 9,768,086 | B2 | 9/2017 | Nuzzo |
| 9,801,557 | B2 | 10/2017 | Ghaffari |
| 9,844,145 | B2 | 10/2017 | Hsu |

(56) References Cited

U.S. PATENT DOCUMENTS

| | | |
|---|---|---|
| 9,810,623 B2 | 11/2017 | Ghaffari |
| 9,833,190 B2 | 12/2017 | Ghaffari |
| 9,839,367 B2 | 12/2017 | Litt |
| 9,846,829 B2 | 12/2017 | Fastert |
| 9,894,757 B2 | 2/2018 | Arora |
| 9,899,330 B2 | 2/2018 | Dalal |
| 9,949,691 B2 | 4/2018 | Huppert |
| 10,032,709 B2 | 7/2018 | Rafferty |
| D825,537 S | 8/2018 | Li |
| 10,064,269 B2 | 8/2018 | Rogers |
| 10,186,546 B2 | 1/2019 | De Graff |
| 10,258,282 B2 | 4/2019 | Huppert |
| 10,277,386 B2 | 4/2019 | Raj |
| 10,296,819 B2 | 5/2019 | Fastert |
| 10,297,572 B2 | 5/2019 | Dalal |
| 10,300,371 B2 | 5/2019 | Ghaffari |
| 10,325,951 B2 | 6/2019 | Graff |
| 10,332,563 B2 | 6/2019 | Lee |
| 10,334,724 B2 | 6/2019 | Hsu |
| 10,374,072 B2* | 8/2019 | Nuzzo ............... H01L 29/78681 |
| 10,383,219 B2 | 8/2019 | Arora |
| 10,398,343 B2 | 9/2019 | Murphy |
| 10,410,962 B2 | 9/2019 | McMahon |
| 10,447,347 B2 | 10/2019 | Raj |
| 10,467,926 B2 | 11/2019 | Ghaffari |
| 10,477,354 B2 | 11/2019 | Patel |
| 10,482,743 B2 | 11/2019 | Li |
| 10,485,118 B2 | 11/2019 | Elolampi |
| 10,532,211 B2 | 1/2020 | Ghaffari |
| 10,567,152 B2 | 2/2020 | Raj |
| 10,653,332 B2 | 5/2020 | McGrane |
| 10,653,342 B2* | 5/2020 | Rogers .................. B01L 3/5027 |
| 10,673,280 B2 | 6/2020 | Raj |
| 10,709,384 B2 | 7/2020 | Sun |
| 10,986,465 B2 | 4/2021 | Patel |
| 2001/0012918 A1 | 8/2001 | Swanson |
| 2001/0021867 A1 | 9/2001 | Kordis |
| 2001/0043513 A1 | 11/2001 | Grupp |
| 2002/0000813 A1 | 1/2002 | Hirono |
| 2002/0019055 A1* | 2/2002 | Brown .................... G01N 33/94 |
| | | 424/449 |
| 2002/0026127 A1 | 2/2002 | Balbierz |
| 2002/0060633 A1 | 5/2002 | Crisco, III |
| 2002/0077534 A1 | 6/2002 | Durousseau |
| 2002/0079572 A1 | 6/2002 | Khan |
| 2002/0082515 A1 | 6/2002 | Campbell |
| 2002/0094701 A1 | 7/2002 | Biegelsen |
| 2002/0107436 A1 | 8/2002 | Barton |
| 2002/0113739 A1 | 8/2002 | Howard |
| 2002/0128700 A1 | 9/2002 | Cross, Jr. |
| 2002/0145467 A1 | 10/2002 | Minch |
| 2002/0151934 A1 | 10/2002 | Levine |
| 2002/0158330 A1 | 10/2002 | Moon |
| 2002/0173730 A1 | 11/2002 | Pottgen |
| 2002/0193724 A1 | 12/2002 | Stebbings |
| 2003/0017848 A1 | 1/2003 | Engstrom |
| 2003/0045025 A1 | 3/2003 | Coyle |
| 2003/0097165 A1 | 5/2003 | Krulevitch |
| 2003/0113827 A1* | 6/2003 | Burkoth ............. A61B 5/14514 |
| | | 436/95 |
| 2003/0120271 A1 | 6/2003 | Burnside |
| 2003/0162507 A1 | 8/2003 | Vatt |
| 2003/0214408 A1 | 11/2003 | Grajales |
| 2003/0227116 A1 | 12/2003 | Halik |
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0118831 A1 | 6/2004 | Martin |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0238819 A1 | 12/2004 | Maghribi |
| 2004/0243204 A1 | 12/2004 | Maghribi |
| 2005/0021103 A1 | 1/2005 | DiLorenzo |
| 2005/0029680 A1 | 2/2005 | Jung |
| 2005/0030408 A1 | 2/2005 | Ito |
| 2005/0065486 A1 | 3/2005 | Fattman |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2005/0204811 A1 | 9/2005 | Neff |
| 2005/0248312 A1 | 11/2005 | Cao |
| 2005/0261617 A1 | 11/2005 | Hall |
| 2005/0258050 A1 | 12/2005 | Bruce |
| 2005/0285262 A1 | 12/2005 | Knapp |
| 2006/0003709 A1 | 1/2006 | Wood |
| 2006/0009700 A1 | 1/2006 | Brumfield |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0122298 A1 | 6/2006 | Menon |
| 2006/0128346 A1 | 6/2006 | Yasui |
| 2006/0154398 A1 | 7/2006 | Qing |
| 2006/0160560 A1 | 7/2006 | Josenhans |
| 2006/0235314 A1 | 10/2006 | Migliuolo |
| 2006/0248946 A1 | 11/2006 | Howell |
| 2006/0257945 A1 | 11/2006 | Masters |
| 2006/0264767 A1 | 11/2006 | Shennib |
| 2006/0270135 A1 | 11/2006 | Chrysler |
| 2006/0276702 A1 | 12/2006 | McGinnis |
| 2006/0286785 A1 | 12/2006 | Rogers |
| 2007/0027374 A1 | 2/2007 | Wihlborg |
| 2007/0027514 A1 | 2/2007 | Gerber |
| 2007/0031283 A1 | 2/2007 | Davis |
| 2007/0069894 A1 | 3/2007 | Lee |
| 2007/0083079 A1 | 4/2007 | Lee |
| 2007/0108389 A1 | 5/2007 | Makela |
| 2007/0113399 A1 | 5/2007 | Kumar |
| 2007/0123756 A1 | 5/2007 | Kitajima |
| 2007/0139451 A1 | 6/2007 | Somasiri |
| 2007/0151358 A1 | 7/2007 | Chien |
| 2007/0179373 A1 | 8/2007 | Pronovost |
| 2007/0190880 A1 | 8/2007 | Dubrow |
| 2007/0196957 A1 | 8/2007 | Akutagawa |
| 2007/0215890 A1 | 9/2007 | Harbers |
| 2007/0270672 A1 | 11/2007 | Hayter |
| 2007/0270674 A1 | 11/2007 | Kane |
| 2008/0008747 A1* | 1/2008 | Royds .................... A61K 9/703 |
| | | 424/449 |
| 2008/0036097 A1 | 2/2008 | Ito |
| 2008/0046080 A1 | 2/2008 | Vanden Bulcke |
| 2008/0074383 A1 | 3/2008 | Dean |
| 2008/0091089 A1 | 4/2008 | Guillory |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0185534 A1 | 8/2008 | Simon |
| 2008/0188912 A1 | 8/2008 | Stone |
| 2008/0190202 A1 | 8/2008 | Kulach |
| 2008/0193749 A1 | 8/2008 | Thompson |
| 2008/0200973 A1 | 8/2008 | Mallozzi |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0262381 A1 | 10/2008 | Kolen |
| 2008/0275327 A1 | 11/2008 | Faarbaek |
| 2008/0287167 A1 | 11/2008 | Caine |
| 2008/0297350 A1 | 12/2008 | Iwasa |
| 2008/0300559 A1 | 12/2008 | Gustafson |
| 2008/0309807 A1 | 12/2008 | Kinoshita |
| 2008/0313552 A1 | 12/2008 | Buehler |

(56) References Cited

U.S. PATENT DOCUMENTS

| | | |
|---|---|---|
| 2009/0000377 A1 | 1/2009 | Shipps |
| 2009/0001550 A1 | 1/2009 | Li |
| 2009/0015560 A1 | 1/2009 | Robinson |
| 2009/0017884 A1 | 1/2009 | Rotschild |
| 2009/0048556 A1 | 2/2009 | Durand |
| 2009/0076363 A1 | 3/2009 | Bly |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0270170 A1 | 10/2009 | Patton |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0317639 A1 | 12/2009 | Axisa |
| 2009/0322480 A1 | 12/2009 | Benedict |
| 2010/0002402 A1 | 1/2010 | Rogers |
| 2010/0030167 A1 | 2/2010 | Thirstrup |
| 2010/0036211 A1 | 2/2010 | La Rue |
| 2010/0041966 A1 | 2/2010 | Kang |
| 2010/0059863 A1 | 3/2010 | Rogers |
| 2010/0063372 A1* | 3/2010 | Potts .................. A61B 5/14521 600/346 |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0234716 A1 | 9/2010 | Engel |
| 2010/0245011 A1 | 9/2010 | Chatzopoulos |
| 2010/0254092 A1 | 10/2010 | Dong |
| 2010/0268112 A1* | 10/2010 | Short .................... G01K 11/16 374/E13.002 |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0019370 A1 | 1/2011 | Koh |
| 2011/0019371 A1 | 1/2011 | Koh |
| 2011/0034760 A1 | 2/2011 | Brynelsen |
| 2011/0034912 A1 | 2/2011 | De Graff |
| 2011/0040157 A1* | 2/2011 | Addington ........ A61M 25/0108 600/301 |
| 2011/0051384 A1 | 3/2011 | Kriechbaum |
| 2011/0054583 A1 | 3/2011 | Litt |
| 2011/0066044 A1 | 3/2011 | Moon |
| 2011/0071603 A1 | 3/2011 | Moore |
| 2011/0098583 A1 | 4/2011 | Pandia |
| 2011/0101789 A1 | 5/2011 | Salter |
| 2011/0121822 A1 | 5/2011 | Parsche |
| 2011/0136436 A1 | 6/2011 | Hoyt |
| 2011/0140856 A1 | 6/2011 | Downie |
| 2011/0140897 A1 | 6/2011 | Purks |
| 2011/0148349 A1 | 6/2011 | Kim |
| 2011/0175735 A1 | 7/2011 | Forster |
| 2011/0184320 A1 | 7/2011 | Shipps |
| 2011/0185611 A1 | 8/2011 | Adams |
| 2011/0193105 A1 | 8/2011 | Lerman |
| 2011/0213559 A1 | 9/2011 | Pollack |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0221580 A1 | 9/2011 | Marsanne |
| 2011/0222375 A1 | 9/2011 | Tsubata |
| 2011/0263950 A1 | 10/2011 | Larson |
| 2011/0270049 A1 | 11/2011 | Katra |
| 2011/0277813 A1 | 11/2011 | Rogers |
| 2011/0284268 A1 | 11/2011 | Palaniswamy |
| 2011/0306851 A1 | 12/2011 | Wang |
| 2011/0317737 A1 | 12/2011 | Klewer |
| 2012/0016258 A1 | 1/2012 | Webster |
| 2012/0028575 A1 | 2/2012 | Chen |
| 2012/0051005 A1 | 3/2012 | Vanfleteren |
| 2012/0052268 A1 | 3/2012 | Axisa |
| 2012/0059235 A1 | 3/2012 | Davies |
| 2012/0065937 A1 | 3/2012 | De Graff |
| 2012/0068848 A1 | 3/2012 | Campbell |
| 2012/0074546 A1 | 3/2012 | Chong |
| 2012/0077441 A1 | 3/2012 | Howard |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0116382 A1 | 5/2012 | Ku |
| 2012/0126418 A1 | 5/2012 | Feng |
| 2012/0150072 A1* | 6/2012 | Revol-Cavalier .... A61B 5/4266 600/573 |
| 2012/0150074 A1 | 6/2012 | Yanev |
| 2012/0150453 A1 | 6/2012 | Benzel |
| 2012/0157804 A1 | 6/2012 | Rogers |
| 2012/0165759 A1 | 6/2012 | Rogers |
| 2012/0172697 A1 | 7/2012 | Urman |
| 2012/0178367 A1 | 7/2012 | Matsumoto |
| 2012/0179075 A1 | 7/2012 | Perry |
| 2012/0206097 A1 | 8/2012 | Scar |
| 2012/0215127 A1 | 8/2012 | Shikida |
| 2012/0220835 A1 | 8/2012 | Chung |
| 2012/0245444 A1 | 9/2012 | Otis |
| 2012/0256308 A1 | 10/2012 | Helin |
| 2012/0256492 A1 | 10/2012 | Song |
| 2012/0294818 A1* | 11/2012 | Fares .................... A61K 8/8176 424/68 |
| 2012/0314382 A1 | 12/2012 | Wesselmann |
| 2012/0316455 A1 | 12/2012 | Rahman |
| 2012/0327608 A1 | 12/2012 | Rogers |
| 2013/0035751 A1 | 2/2013 | Shalev |
| 2013/0041235 A1 | 2/2013 | Rogers |
| 2013/0044215 A1 | 2/2013 | Rothkopf |
| 2013/0066365 A1 | 3/2013 | Belson |
| 2013/0079693 A1 | 3/2013 | Ranky |
| 2013/0085552 A1 | 4/2013 | Mandel |
| 2013/0099358 A1 | 4/2013 | Elolampi |
| 2013/0100618 A1 | 4/2013 | Rogers |
| 2013/0116520 A1 | 5/2013 | Roham |
| 2013/0118255 A1 | 5/2013 | Callsen |
| 2013/0123587 A1 | 5/2013 | Sarrafzadeh |
| 2013/0131540 A1* | 5/2013 | Fredericks ............... A61B 5/01 600/549 |
| 2013/0131660 A1 | 5/2013 | Monson |
| 2013/0147063 A1 | 6/2013 | Park |
| 2013/0185003 A1 | 7/2013 | Carbeck |
| 2013/0192356 A1 | 8/2013 | De Graff |
| 2013/0197319 A1 | 8/2013 | Monty |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0237150 A1 | 9/2013 | Royston |
| 2013/0245387 A1 | 9/2013 | Patel |
| 2013/0245388 A1 | 9/2013 | Rafferty |
| 2013/0253285 A1 | 9/2013 | Bly |
| 2013/0261415 A1 | 10/2013 | Ashe |
| 2013/0261464 A1 | 10/2013 | Singh |
| 2013/0285836 A1 | 10/2013 | Proud |
| 2013/0313713 A1 | 11/2013 | Arora |
| 2013/0316442 A1 | 11/2013 | Meurville |
| 2013/0316487 A1 | 11/2013 | De Graff |
| 2013/0316645 A1 | 11/2013 | Li |
| 2013/0320503 A1 | 12/2013 | Nuzzo |
| 2013/0321373 A1 | 12/2013 | Yoshizumi |
| 2013/0325357 A1 | 12/2013 | Walerow |

(56) References Cited

U.S. PATENT DOCUMENTS

| | | |
|---|---|---|
| 2013/0328219 A1 | 12/2013 | Chau |
| 2013/0331914 A1 | 12/2013 | Lee |
| 2013/0335011 A1 | 12/2013 | Bohringer |
| 2014/0001058 A1 | 1/2014 | Ghaffari |
| 2014/0002242 A1 | 1/2014 | Fenkanyn |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0081100 A1 | 3/2014 | Muhsin |
| 2014/0097944 A1 | 4/2014 | Fastert |
| 2014/0108842 A1 | 4/2014 | Frank |
| 2014/0110859 A1 | 4/2014 | Rafferty |
| 2014/0125458 A1 | 5/2014 | Bachman |
| 2014/0140020 A1 | 5/2014 | Rogers |
| 2014/0188426 A1 | 7/2014 | Fastert |
| 2014/0191236 A1 | 7/2014 | Nuzzo |
| 2014/0206976 A1 | 7/2014 | Thompson |
| 2014/0216524 A1 | 8/2014 | Rogers |
| 2014/0257427 A1 | 9/2014 | Marnfeldt |
| 2014/0275823 A1* | 9/2014 | Lane ............... A61B 5/259 600/372 |
| 2014/0275835 A1 | 9/2014 | Lamego |
| 2014/0303452 A1 | 10/2014 | Ghaffari |
| 2014/0303520 A1 | 10/2014 | Telfort |
| 2014/0303680 A1 | 10/2014 | Donnelly |
| 2014/0308930 A1 | 10/2014 | Tran |
| 2014/0316191 A1 | 10/2014 | De Zambotti |
| 2014/0316192 A1 | 10/2014 | de Zamboti |
| 2014/0318699 A1 | 10/2014 | Longinotti-Buitoni |
| 2014/0340857 A1 | 11/2014 | Hsu |
| 2014/0342174 A1 | 11/2014 | Tominaga |
| 2014/0343371 A1* | 11/2014 | Sowers, II ......... A61B 5/1455 600/323 |
| 2014/0350883 A1 | 11/2014 | Carter |
| 2014/0371547 A1 | 12/2014 | Gartenberg |
| 2014/0371823 A1 | 12/2014 | Mashiach |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0025394 A1 | 1/2015 | Hong |
| 2015/0035743 A1 | 2/2015 | Rosener |
| 2015/0057515 A1* | 2/2015 | Hagen ............. G01N 27/3273 205/792 |
| 2015/0100135 A1 | 4/2015 | Ives |
| 2015/0116814 A1 | 4/2015 | Takakura |
| 2015/0126878 A1 | 5/2015 | An |
| 2015/0141775 A1* | 5/2015 | Macaluso ......... A61B 10/0064 600/307 |
| 2015/0145676 A1 | 5/2015 | Adhikari |
| 2015/0150505 A1 | 6/2015 | Kaskoun |
| 2015/0164377 A1 | 6/2015 | Nathan |
| 2015/0178806 A1 | 6/2015 | Nuzzo |
| 2015/0181700 A1 | 6/2015 | Rogers |
| 2015/0194817 A1 | 7/2015 | Lee |
| 2015/0237711 A1 | 8/2015 | Rogers |
| 2015/0241288 A1 | 8/2015 | Keen |
| 2015/0248833 A1 | 9/2015 | Arne |
| 2015/0272652 A1 | 10/2015 | Ghaffari |
| 2015/0335254 A1 | 11/2015 | Fastert |
| 2015/0359458 A1* | 12/2015 | Erickson ............. G06T 7/90 382/133 |
| 2015/0359469 A1* | 12/2015 | Jacobs ............. A61B 5/6824 600/362 |
| 2015/0371511 A1 | 12/2015 | Miller |
| 2015/0373487 A1 | 12/2015 | Miller |
| 2016/0006123 A1 | 1/2016 | Li |
| 2016/0015962 A1 | 1/2016 | Shokoueinejad Maragheh |
| 2016/0037478 A1 | 2/2016 | Skaaksrud |
| 2016/0049824 A1 | 2/2016 | Stein |
| 2016/0051156 A1 | 2/2016 | Kim |
| 2016/0058380 A1 | 3/2016 | Lee |
| 2016/0066854 A1 | 3/2016 | Mei |
| 2016/0081563 A1 | 3/2016 | Wiard |
| 2016/0086909 A1 | 3/2016 | Garlock |
| 2016/0095652 A1 | 4/2016 | Lee |
| 2016/0099214 A1 | 4/2016 | Dalal |
| 2016/0099227 A1 | 4/2016 | Dalal |
| 2016/0111353 A1 | 4/2016 | Rafferty |
| 2016/0135740 A1 | 5/2016 | Ghaffari |
| 2016/0150839 A1* | 6/2016 | Allen ............... A41D 19/0058 2/161.6 |
| 2016/0178251 A1 | 6/2016 | Johnson |
| 2016/0213262 A1 | 7/2016 | Ghaffari |
| 2016/0213424 A1 | 7/2016 | Ghaffari |
| 2016/0220184 A1* | 8/2016 | Manion ............. A61B 5/4266 |
| 2016/0228640 A1 | 8/2016 | Pindado |
| 2016/0240061 A1 | 8/2016 | Li |
| 2016/0249174 A1 | 8/2016 | Patel |
| 2016/0256070 A1 | 9/2016 | Murphy |
| 2016/0271290 A1 | 9/2016 | Humayun |
| 2016/0284544 A1 | 9/2016 | Nuzzo |
| 2016/0287177 A1 | 10/2016 | Huppert |
| 2016/0293794 A1 | 10/2016 | Nuzzo |
| 2016/0309594 A1 | 10/2016 | Hsu |
| 2016/0310306 A1* | 10/2016 | Brister ............. A61B 5/6871 |
| 2016/0322283 A1 | 11/2016 | McMahon |
| 2016/0338646 A1 | 11/2016 | Lee |
| 2016/0361015 A1 | 12/2016 | Wang |
| 2016/0371957 A1 | 12/2016 | Ghaffari |
| 2016/0381789 A1 | 12/2016 | Rogers |
| 2017/0027482 A1* | 2/2017 | Zilberstein ......... A61B 5/14546 |
| 2017/0071491 A1 | 3/2017 | Litt |
| 2017/0079588 A1 | 3/2017 | Ghaffari |
| 2017/0079589 A1 | 3/2017 | Ghaffari |
| 2017/0081471 A1* | 3/2017 | Chou ............... C08G 69/14 |
| 2017/0083312 A1 | 3/2017 | Pindado |
| 2017/0086747 A1 | 3/2017 | Ghaffari |
| 2017/0086748 A1 | 3/2017 | Ghaffari |
| 2017/0086749 A1 | 3/2017 | Ghaffari |
| 2017/0100102 A1* | 4/2017 | Heikenfeld ......... A61B 5/14521 |
| 2017/0105621 A1* | 4/2017 | Pratt ............... G16H 50/20 |
| 2017/0105795 A1 | 4/2017 | Lee |
| 2017/0110417 A1 | 4/2017 | Arora |
| 2017/0116492 A1* | 4/2017 | Bukshpan ........... A61B 5/1171 |
| 2017/0164865 A1 | 6/2017 | Rafferty |
| 2017/0164866 A1 | 6/2017 | Rafferty |
| 2017/0181659 A1 | 6/2017 | Rafferty |
| 2017/0186727 A1 | 6/2017 | Dalal |
| 2017/0188942 A1 | 7/2017 | Ghaffari |
| 2017/0200670 A1 | 7/2017 | Rafferty |
| 2017/0200679 A1 | 7/2017 | Rogers |
| 2017/0200707 A1 | 7/2017 | Rogers |
| 2017/0224257 A1* | 8/2017 | Rogers ............. A61B 5/0537 |
| 2017/0231571 A1* | 8/2017 | Rogers ............. A61B 5/1455 600/301 |
| 2017/0296114 A1 | 10/2017 | Ghaffari |
| 2017/0331524 A1 | 11/2017 | Aranyosi |
| 2017/0340236 A1 | 11/2017 | Ghaffari |
| 2018/0064377 A1* | 3/2018 | Rogers ............. B01L 3/5027 |
| 2018/0076336 A1 | 3/2018 | Graff |
| 2018/0111353 A1 | 4/2018 | Huppert |
| 2018/0192918 A1 | 7/2018 | Ives |
| 2018/0199884 A1 | 7/2018 | Huppert |
| 2018/0293472 A1 | 10/2018 | Fastert |
| 2018/0302980 A1 | 10/2018 | Arora |
| 2018/0302988 A1 | 10/2018 | Hsu |
| 2018/0308799 A1 | 10/2018 | Dalal |
| 2019/0154723 A1 | 5/2019 | Kacyvenski |
| 2019/0265168 A1 | 8/2019 | Huppert |
| 2019/0314192 A1 | 10/2019 | Raj |
| 2019/0365263 A1 | 12/2019 | Raj |
| 2020/0060618 A1 | 2/2020 | Davis |
| 2020/0088739 A1* | 3/2020 | Rogers ............. A61B 10/0064 |
| 2020/0187349 A1 | 6/2020 | Lee |
| 2020/0281082 A1 | 9/2020 | Elolampi |

(56) References Cited

U.S. PATENT DOCUMENTS

| | | |
|---|---|---|
| 2020/0296543 A1 | 9/2020 | Patel |
| 2021/0068677 A1 | 3/2021 | Raj |

FOREIGN PATENT DOCUMENTS

| | | |
|---|---|---|
| CN | 102772246 A | 11/2012 |
| CN | 103165478 A | 6/2013 |
| CN | 103313671 A | 9/2013 |
| CN | 103619590 A | 3/2014 |
| DE | 10 2006 011 596 A1 | 9/2007 |
| DE | 10 2006 051 745 A1 | 5/2008 |
| DE | 10 2007 046 886 A1 | 4/2009 |
| DE | 10 2008 044 902 A1 | 3/2010 |
| EP | 0526855 A1 | 2/1993 |
| EP | 0585670 A2 | 3/1994 |
| EP | 0779059 A1 | 6/1997 |
| EP | 0952542 A1 | 10/1999 |
| EP | 1100296 A1 | 5/2001 |
| EP | 1188157 A1 | 3/2002 |
| EP | 1671581 A1 | 6/2006 |
| EP | 1808124 A2 | 7/2007 |
| EP | 2259062 A2 | 12/2010 |
| EP | 2498196 A2 | 9/2012 |
| EP | 2541995 A1 | 1/2013 |
| GB | 2521714 A | 7/2015 |
| JP | H 04-290489 A | 10/1992 |
| JP | 05-087511 A | 4/1993 |
| JP | H 05-102228 A | 4/1993 |
| JP | 9-201338 A | 8/1997 |
| JP | H10-155753 A | 6/1998 |
| JP | 2001-156278 A | 6/2001 |
| JP | 03-218797 B2 | 10/2001 |
| JP | 2002-90479 A | 3/2002 |
| JP | 2002-263185 A | 9/2002 |
| JP | 2003-046291 A | 2/2003 |
| JP | 2005-052212 A | 3/2005 |
| JP | 2006-520657 A | 9/2006 |
| JP | 2006-523127 A | 10/2006 |
| JP | 2007-042829 A | 2/2007 |
| JP | 2007-502136 A | 2/2007 |
| JP | 2008-194323 A | 8/2008 |
| JP | 2009-150590 A | 7/2009 |
| JP | 2009-158839 A | 7/2009 |
| JP | 2009-170173 A | 7/2009 |
| JP | 2011-082050 A | 4/2011 |
| JP | 2011-103914 A | 6/2011 |
| JP | 2011-122732 A | 6/2011 |
| JP | 2012-134272 A | 7/2012 |
| JP | 2012-515436 A | 7/2012 |
| JP | 2013-089959 A | 5/2013 |
| JP | 2013-128060 A | 6/2013 |
| JP | 2013-130384 A | 7/2013 |
| JP | 2013-536592 A | 9/2013 |
| WO | WO 1999/038211 A2 | 7/1999 |
| WO | WO 1999/059646 A1 | 11/1999 |
| WO | WO 2000/079497 A1 | 12/2000 |
| WO | WO 2002/17362 A2 | 2/2002 |
| WO | WO 2002/047162 A2 | 6/2002 |
| WO | WO 2003/021679 A2 | 3/2003 |
| WO | WO 2004/084720 A2 | 10/2004 |
| WO | WO 2005/083546 A1 | 9/2005 |
| WO | WO 2005/122285 A2 | 12/2005 |
| WO | WO 2006/013573 A2 | 2/2006 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2008/055212 A2 | 5/2008 |
| WO | WO 2008/069682 A1 | 6/2008 |
| WO | WO 2008/143635 A1 | 11/2008 |
| WO | WO 2009/008892 A1 | 1/2009 |
| WO | WO 2009/036260 A1 | 3/2009 |
| WO | WO 2009/111641 A1 | 9/2009 |
| WO | WO 2009/114689 A1 | 9/2009 |
| WO | WO 2009/135070 A1 | 11/2009 |
| WO | WO 2010/029966 A1 | 3/2010 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/117862 A2 | 9/2011 |
| WO | WO 2011/124898 A1 | 10/2011 |
| WO | WO 2011/127331 A2 | 10/2011 |
| WO | WO 2012/094264 A2 | 7/2012 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/059671 A1 | 4/2013 |
| WO | WO 2013/063634 A1 | 5/2013 |
| WO | WO 2013/144738 A2 | 10/2013 |
| WO | WO 2013/144866 A1 | 10/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/124044 A1 | 8/2014 |
| WO | WO 2014/124049 A2 | 8/2014 |
| WO | WO 2014/130928 A2 | 8/2014 |
| WO | WO 2014/130931 A1 | 8/2014 |
| WO | WO 2014/179343 A1 | 11/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/120330 A1 | 8/2015 |
| WO | WO 2015/127458 A1 | 8/2015 |
| WO | WO 2015/134588 A1 | 9/2015 |
| WO | WO 2015/138712 A1 | 9/2015 |
| WO | WO 2015/145471 A1 | 10/2015 |
| WO | WO 2015/159280 | 10/2015 |
| WO | WO 2015/159280 A1 | 10/2015 |
| WO | WO 2016/010983 A1 | 1/2016 |
| WO | WO 2016/025430 | 2/2016 |
| WO | WO 2016/025430 A1 | 2/2016 |
| WO | WO 2016/025468 A2 | 2/2016 |
| WO | WO 2016/026028 A1 | 2/2016 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |
| WO | WO 2016/127050 A1 | 8/2016 |
| WO | WO 2016/134306 A1 | 8/2016 |
| WO | WO 2016-140961 A1 | 9/2016 |
| WO | WO 2016/149583 A1 | 9/2016 |
| WO | WO 2016/205385 A1 | 12/2016 |
| WO | WO 2017/015000 A1 | 1/2017 |
| WO | WO 2017/059215 A1 | 4/2017 |
| WO | WO 2017/062508 A1 | 4/2017 |
| WO | WO 2017/184705 A1 | 10/2017 |
| WO | WO 2018/013569 A1 | 1/2018 |
| WO | WO 2018/013656 A1 | 1/2018 |

(56) References Cited

FOREIGN PATENT DOCUMENTS

| WO | WO 2018/057911 A1 | 3/2018 |
|---|---|---|
| WO | WO 2015/077559 A1 | 5/2018 |
| WO | WO 2018/081778 A1 | 5/2018 |
| WO | WO 2018/085336 A1 | 5/2018 |
| WO | WO 2018/093751 A1 | 5/2018 |
| WO | WO 2018/119193 A1 | 6/2018 |
| WO | WO 2018/136462 A1 | 7/2018 |
| WO | WO 2018/208523 A1 | 11/2018 |

OTHER PUBLICATIONS

Demura et al., "Immobilization of Glucose Oxidase with *Bombyx Mori* Silk Fibroin by Only Stretching Treatment and its Application to Glucose Sensor," Biotechnology and Bioengineering, vol. 33, 598-603 (6 pages) (1989).
Ellerbee et al., "Quantifying Colorimetric Assays in Paper-Based Microfluidic Devices by Measuring the Transmission of Light through Paper," Analytical Chemistry, vol. 81, No. 208447-8452, (6 pages) (Oct. 15, 2009).
Halsted, "Ligature and Suture Material," Journal of the American Medical Association, vol. LX, No. 15, 1119-1126, (8 pages) (Apr. 12, 1913).
Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).
Kim et al., "Dissolvable Films of Silk Fibroin for Ultrathin Conformal Bio-Integrated Electronics," Nature, 1-8 (8 pages) (Apr. 18, 2010).
Kim et al., "Materials and Noncoplanar Mesh Designs for Integrated Circuits With Linear Elastic Responses to Extreme Mechanical Deformations," PNAS, vol. 105, No. 48, 18675-18680 (6 pages) (Dec. 2, 2008).
Kim et al., "Stretchable and Foldable Silicon Integrated Circuits," Science, vol. 320, 507-511 (5 pages) (Apr. 25, 2008).
Kim et al., "Electrowetting on Paper for Electronic Paper Display," ACS Applied Materials & Interfaces, vol. 2, No. 11, (3318-3323) (6 pages) (Nov. 24, 2010).
Ko et al., "A Hemispherical Electronic Eye Camera Based on Compressible Silicon Optoelectronics," Nature, vol. 454, 748-753 (6 pages) (Aug. 7, 2008).
Lawrence et al., "Bioactive Silk Protein Biomaterial Systems for Optical Devices," Biomacromolecules, vol. 9, 1214-1220 (7 pages) (Nov. 4, 2008).
Meitl et al., "Transfer Printing by Kinetic Control of Adhesion to an Elastomeric Stamp," Nature, vol. 5, 33-38 (6 pages) (Jan. 2006).
Omenetto et al., "A New Route for Silk," Nature Photonics, vol. 2, 641-643 (3 pages) (Nov. 2008).
Omenetto et al., "New Opportunities for an Ancient Material," Science, vol. 329, 528-531 (5 pages) (Jul. 30, 2010).
Siegel et al., "Foldable Printed Circuit Boards on Paper Substrates," Advanced Functional Materials, vol. 20, No. 1, 28-35, (8 pages) (Jan. 8, 2010).
Tsukada et al., "Structural Changes of Silk Fibroin Membranes Induced by Immersion in Methanol Aqueous Solutions," Journal of Polymer Science, vol. 32, 961-968 (8 pages) (1994).
Wang et al., "Controlled Release From Multilayer Silk Biomaterial Coatings to Modulate Vascular Cell Responses" Biomaterials, 29, 894-903 (10 pages) (Nov. 28, 2008).
Wikipedia, "Ball bonding" article [online]. Cited in PCT/US2015/051210 search report dated Mar. 1, 2016 with the following information "Jun. 15, 2011 [retrieved on Nov. 15, 2015}. Retrieved 12-18, 29 from the Internet: <URL: https://web.archive.org/web/20110615221003/hltp://en.wikipedia.org/wiki/Ball_bonding>., entire document, especially para 1, 4, 5, 6," 2 pages, last page says ("last modified on May 11, 2011").
Bossuyt et al., "Stretchable Electronics Technology for Large Area Applications: Fabrication and Mechanical Characterizations", vol. 3, pp. 229-235 (7 pages) (Feb. 2013).
Jones et al., "Stretchable Interconnects for Elastic Electronic Surfaces". vol. 93, pp. 1459-1467 (9 pages) (Aug. 2005).
Lin et al., "Design and Fabrication of Large-Area, Redundant, Stretchable Interconnect Meshes Using Excimer Laser Photoablation and In Situ Masking", (10 pages) (Aug. 2010).
Kim et al., "A Biaxial Stretchable Interconnect With Liquid-Alloy-Covered Joints on Elastomeric Substrate", vol. 18, pp. 138-146 (9 pages) (Feb. 2009).
Kinkeldi et al., "Encapsulation for Flexible Electronic Devices", IEE Electron Device Letters, 32(12):1743-5 (2011).
Hsu et al., "Epidermal electronics: Skin sweat patch", Microsystems, Packaging, Assembly and Circuits Technology Conference (IMPACT), 2012 7th International. IEEE, 2012.
Siegel et al., "Foldable printed circuit boards on paper substrates", Advanced Functional Materials, 20:28-35 (2010).
Ellerbee et al., "Quantifying colorimetric assays in paper-based microfluidic devices by measuring the transmission of light through paper", Anal. Chem.,81(20):8447-52 (2009).
Wehner et al.; "A Lightweight Soft Exosuit for Gait Assistance"; IEEE International Conference on Robotics and Automation (ICRA), May 6-10, 2013. Retrieved from https://micro.seas.harvard.edu/papers/Wehner_ICRA13.pdf (8 pages).
Cauwe et al., "Flexible and Stretchable Circuit Technologies For Space Applications," 5th Electronic Materials, Processes and Packaging for Space, May 20-22, 2014 (18 pages).
Hild, "Surface Energy of Plastics," Dec. 16, 2009. Retrieved from https://www.tstar.com/blog/bid/33845/surface-energy-of-plastics (3 pages).
Hodge et al., "A Microcolorimetric Method for the Determination of Chloride," Microchemical Journal, vol. 7, Issue 3, Sep. 30, 1963, pp. 326-330 (5 pages).
Bonifácio et al., "An improved flow system for chloride determination in natural waters exploiting solid-phase reactor and long pathlength spectrophotometry," Talanta, vol. 72, Issue 2, Apr. 30, 2007, pp. 663-667 (5 pages).
Meyer et al., "The Effect of Gelatin Cross-Linking on the Bioequivalence of Hard and Soft Gelatin Acetaminophen Capsules," Pharmaceutical Research, vol. 17, No. 8, Aug. 31, 2000, pp. 962-966 (5 pages).
Bang et al.; "The Smart House for Older Persons and Persons With Disabilities: Structure, Technology Arrangements, and Perspectives"; IEEE Transactions on Neural Systems and Rehabilitation Engineering, IEEE Service Center, New York, New York; vol. 12, No. 2, pp. 228-250; Jun. 1, 2004; XP011113818; ISSN: 1534-4320 (23 pages).
Duan et al.; "High Performance thin-film transistors using semiconductor nanowires and nanoribbons"; Nature, vol. 425, pp. 274-278; Sep. 2003 (5 pages).
J. Kim et al.; "Miniaturized Flexible Electronic Systems with Wireless Power and Near-Field Communication Capabilities"; Advanced Function Materials, 2015, vol. 25, pp. 4761-4767; XP55420377 (7 pages).
V. Curto et al.; "Wearable Micro-Fluidic pH Sweat Sensing Device Based on Colorimetric Imaging Technologies"; 15th International Conference on Miniaturized Systems for Chemistry and Life Sciences, Oct. 2, 2011; pp. 577-579; XP55525572 (3 pages).
J. Kim et al.; "Epidermal Electronics with Advanced Capabilities in Near-Field Communication"; Small, vol. 11, No. 8, pp. 906-912; Feb. 1, 2015; XP055632692 (7 pages).
Lin Hao et al.; "Noninvasive and Continuous Blood Pressure Monitoring Using Wearable Body Sensor Networks"; IEEE Intelligent Systems, IEEE, US, vol. 30, No. 6, pp. 38-48; Sep. 23, 2015; XP011589366 (11 pages).
J. Franco et al.; "Continuous, Non-invasive and Cuff-free Blood Pressure Monitoring System"; Andean Region International Conference, 2012 VI, IEEE, Nov. 7, 2012; pp. 31-34; XP032419437 (4 pages).
Dieffenderfer, J. et al.; "Wearable wireless sensors for chronic respiratory disease monitoring"; 2015 IEEE 12th international Conference on Wearable and implantable Body Sensor Networks (BSN), IEEE, Jun. 9, 2015; pp. 1-6; XP032795084; DOI: 10.1109/BSN.2015.7299411 (6 pages).
Yuhao et al.; "Epidermal mechano-acoustic sensing electronics for cardiovascular diagnostics and human-machine interfaces"; Science

(56) References Cited

OTHER PUBLICATIONS

Advances, pp. e1601185-1; Nov. 16, 2016; XP055572742; DOI: 10.1126/sciadv.1601185 (13 pages).

Curto, V. F. et al., "Wearable micro-fluidic pH sweat sensing device based on colorimetric imaging techniques," 15$^{th}$ International Conference Omninaturized Systems for Chemistry and Life Sciences, Oct. 2, 2011, pp. 577-579.

Curto et al., "Real-time sweat pH monitoring based on a wearable chemical barcode micro-fluidic platform incorporating ionic liquids," Sensors and Actuators B, vol. 171-172, Jul. 3, 2012, pp. 1327-1334.

Kim, J. et al., "Epidermal Electronics with Advanced Capabilities in Near-Field Communication," Small, vol. 11, No. 8, Feb. 1, 2015, pp. 906-912.

Kim, J. et al., "Miniaturized Flexible Electronic Systems with Wireless Power and Near-Field Communication Capabilities," Advanced Functional Materials, vol. 25, No. 30, Jun. 28, 2015, pp. 4761-4767.

Extended European Search Report for European Patent Application No. EP 17786536.7 , dated Oct. 25, 2019 (13 pages).

\* cited by examiner

METHOD AND SYSTEM FOR MEASURING PERSPIRATION

CROSS-REFERENCE TO RELATED APPLICATIONS

The present application is a division of U.S. Non-Provisional application Ser. No. 15/491,379, filed Apr. 19, 2017, now allowed, which claims the benefit of and priority to U.S. Provisional Application No. 62/324,723, filed Apr. 19, 2016, entitled, "METHOD AND SYSTEM FOR MEASURING PERSPIRATION," each of which is hereby incorporated by reference herein in its entirety.

BACKGROUND

Technical Field of the Invention

The present invention is directed to methods and systems for measuring perspiration. More specifically, the present invention is directed to methods and systems for quantitatively measuring the volume and rate of perspiration as well as quantitatively measuring biochemical elements found in perspiration.

Description of the Prior Art

Typical systems for measuring perspiration or sweat are found in laboratories that collect perspiration in highly controlled environments and perform subsequent analyses using conventional chemical analysis techniques such as mass spectroscopy and biochemical assays.

SUMMARY

The present invention is directed to methods and systems for quantitatively determining the volume and rate of perspiration, and for detecting and quantitatively determining specific biochemical elements present in perspiration of a user.

In accordance with implementations of the invention, a sensor patch can include a perspiration volume sensing channel and a perspiration component sensing chamber. The channel can include at least a first colorimetric material that changes color in response to exposure to perspiration. The chamber can include at least a second colorimetric material that changes color in response to exposure to a biochemical component in the perspiration. The patch can include a near field communication circuit.

In accordance with implementations of the invention, a method of using a smart device and a sensor patch placed on a surface of a user to determine one or more properties of perspiration from the user includes causing the smart device to interrogate a near field communication circuit of the sensor patch. The near field communication circuit (NFC) and/or the NFC antenna can be included in a near field communication chip or other integrated circuit chip or device. The method further includes executing a function on the smart device to obtain at least one image of the sensor patch based on data sent from the near field communication circuit in response to the interrogation. The method further includes analyzing the at least one image to determine a volume of the perspiration, a rate of the perspiration, one or more components within the perspiration, or a combination thereof.

In accordance with implementations of the invention, a sensor patch includes at least one perspiration sensing portion and a near field communication circuit. The portion can include at least one colorimetric material that changes color in response to perspiration. The near field communication circuit (NFC) and/or the NFC antenna can be included in a near field communication chip or other integrated circuit chip or device. The near field communication circuit can be configured to cause a smart device to execute a function on the smart device based on data sent from the near field communication circuit in response to interrogation of the near field communication circuit by the smart device.

These and other capabilities of the invention, along with the invention itself, will be more fully understood after a review of the following figures, detailed description, and claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions.

DETAILED DESCRIPTION OF PREFERRED EMBODIMENTS

The present invention is directed to methods and systems for quantitatively determining the volume and rate of perspiration, and for detecting and quantitatively determining specific biochemical elements present in perspiration of a user. The system can include a sensor patch adhered to the body and a mobile device, such as a smart phone. The method can include taking an image (e.g., a photograph or video) of the sensor patch prior to beginning the activity that results in perspiration and then taking an image (e.g., a photograph or video) of the sensor patch prior to during or after completing the activity that results in perspiration. A comparison of the images, including images of various sections of the sensor patch can be used to determine, quantitatively, the volume and rate of perspiration as well as detect the presence and amount of biochemical components, such as sodium ions, chloride ions, glucose, and lactate in the perspiration. The pH and other chemical properties of the perspiration can also be detected.

Figure 1A:
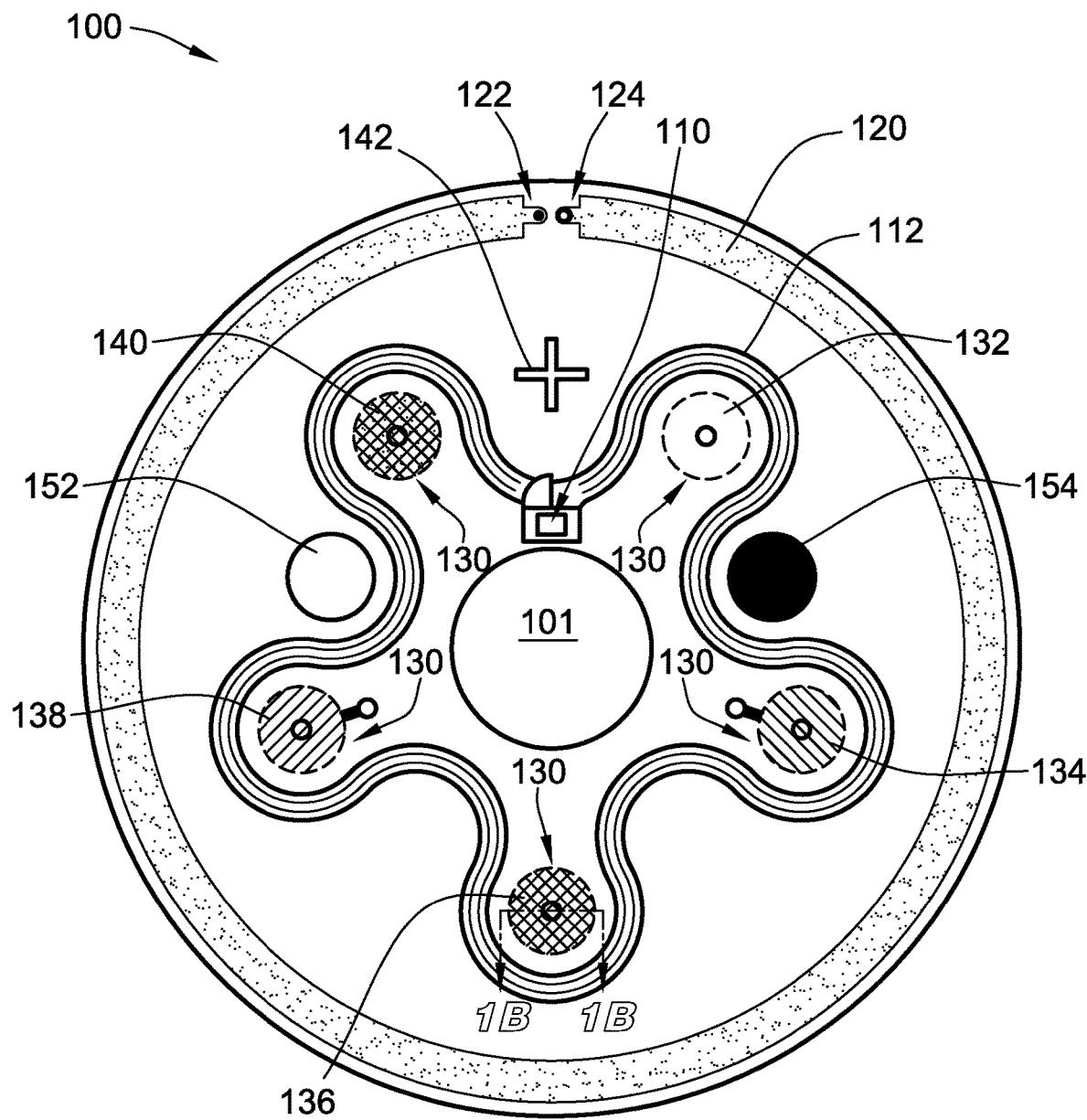
FIG. 1A shows a diagrammatic top view of a sensor patch 100 according to some embodiments of the invention.

FIG. 1A shows a diagrammatic top view of a sensor patch 100 according to some embodiments of the invention. The sensor patch 100 can include a near field communication (NFC) IC chip 110 (which can include an NFC circuit and/or an NFC antenna 112), a perspiration volume (and rate) sensing channel 120, and one or more sensing chambers 130 for detecting and quantifying biochemical components of perspiration and/or pH. Although, in some embodiments of the invention, one of the perspiration volume sensing channel 120 or the one or more sensing chambers 130 can be omitted. A biocompatible adhesive layer (FIG. 2A) can be used to adhere the sensor patch 100 to the skin, although, the patch 100 can be integrated into a layer of clothing to hold it in position without the need for adhesives. The sensor patch 100 can also include printed indicia, including registration marks 142 and color reference marks 152, 154, to facilitate imaging of the sensor patch 100. The central section of the sensor patch 100 can include an opening or hole 101 to reduce the amount of skin surface area being covered and allow perspiration to escape.

As discussed above, the sensor patch 100 also can include multiple sensing portions for detecting and quantifying components of a fluid and/or parameters (e.g., pH) within a fluid. In preferred embodiments of the invention, the fluid can be perspiration of a user on which the sensor patch 100 is placed and the components can be one or more biological components. In some embodiments of the invention, the sensing portions can include a perspiration volume (and rate) sensing channel 120 for detecting the volume and/or rate of perspiration. The sensing portions can also include one or more sensing chambers 130 for detecting and quantifying biochemical components of perspiration and/or biochemical parameters (e.g., pH).

The perspiration volume sensing channel 120 can be a single channel. Alternative, the perspiration volume sensing channel 120 can include multiple perspiration channels. The perspiration volume sensing channel 120 can include a colorimetric coating that changes color in the presence of perspiration. In some embodiments, the coating can be, for example, silver chloranilate. One surface of the sensor patch 100 can be configured to contact the surface (e.g., skin) of a user and can include a channel inlet port 122 that is in fluidic communication with the one or more perspiration channels. The channel inlet port 122 allows perspiration flow from the skin of the user to the one or more channels of the perspiration volume sensing channel 120. A channel vent port 124 can optionally be provided to reduce the backpressure within the perspiration volume sensing channel 120 as the perspiration flows into the perspiration volume sensing channel 120.

The sensor patch 100 as a whole, or one or more layers of the sensor patch 100, can be formed of a transparent material that enables the user to see the color change through the top of the sensor patch 100. The color change starts at the area of the perspiration volume sensing channel 120 closest to the channel inlet port 122 and advances with time toward the channel vent port 124. Based on the known volume of the perspiration volume sensing channel 120 and the length of the color change in the perspiration volume sensing channel 120, a measure of the volume of perspiration can be determined. Based on the elapsed time from a first point in time, such as the beginning of the perspiration entering the perspiration volume sensing channel 120, to a later point in time, such as when the perspiration reaches the vent port 124 or any point along the perspiration volume sensing channel 120, the rate of perspiration can be determined.

While the perspiration volume sensing channel 120 is shown as following the outer perimeter of the sensor patch 100, the perspiration volume sensing channel 120 can be any shape, including a straight line or set of straight lines, a zigzag shape, a serpentine shape, a spiral pattern, or a combination of different shapes and/or patterns. The perspiration volume sensing channel 120 can also be on any area of the sensor patch 100, not necessarily the perimeter. Longer or shorter patterns can be provided depending on the desired longer or shorter useful life of the perspiration volume sensing channel 120 and/or sensor patch 100.

The sensing chambers 130 can be used to detect and measure the quantity of various biochemical components found in and/or properties of (e.g., pH) the user's perspiration. Each sensing chamber 130 can include one or more inlet ports (shown in FIG. 2B) that enable perspiration to enter the sensing chambers 130 and a vent port (shown in FIGS. 2C and 2D) that reduce the back pressure within the sensing chambers 130. Each sensing chamber 130 can include an absorbent substrate material (e.g., cellulose or fabric) that carries a colorimetric assay or color sensitive material 132, 134, 136, 138, and 140 that changes color in response to the presence of a biochemical component, such as sodium ions, chloride ions, glucose, lactate, alcohol, potassium, or in response to a property of the perspiration, such as the pH of the perspiration. Other colorimetric assays, such as for detecting illegal drugs or biomarkers indicative of illegal drug use can also be used. The absorbent substrate material can be formed from one or more of the following materials, including porous absorbent paper, open-cell or closed-cell foam, woven or non-woven fabrics, microfiber cloth, and nano-fiber mesh.

The sensor patch 100 can be constructed of individual layers of stretchable and/or flexible polymeric biocompatible materials, such as silicone elastomers (e.g., PDMS), polyurethane, polyimide and acrylic adhesive materials. Low modulus of elasticity formulations (less than 2 MPa) of these materials can be used to create a very thin sensor patch 100 having a thickness of less than about 2 mm and preferably in the range from about 250 µm to about 1000 µm. Various areas can be functionalized to improve performance of the sensor patch 100. For example, the inlet port 122 described above (and those described below) can include an absorbent material or coating that attracts perspiration (e.g., hydrophilic material or coating, such as PEG, cellulose, or paper).

A biocompatible adhesive layer can be used to adhere the sensor patch 100 to the skin, although, the sensor patch 100 alternatively can be integrated into a layer of clothing to hold it in position without the need for adhesives.

Figure 1B:
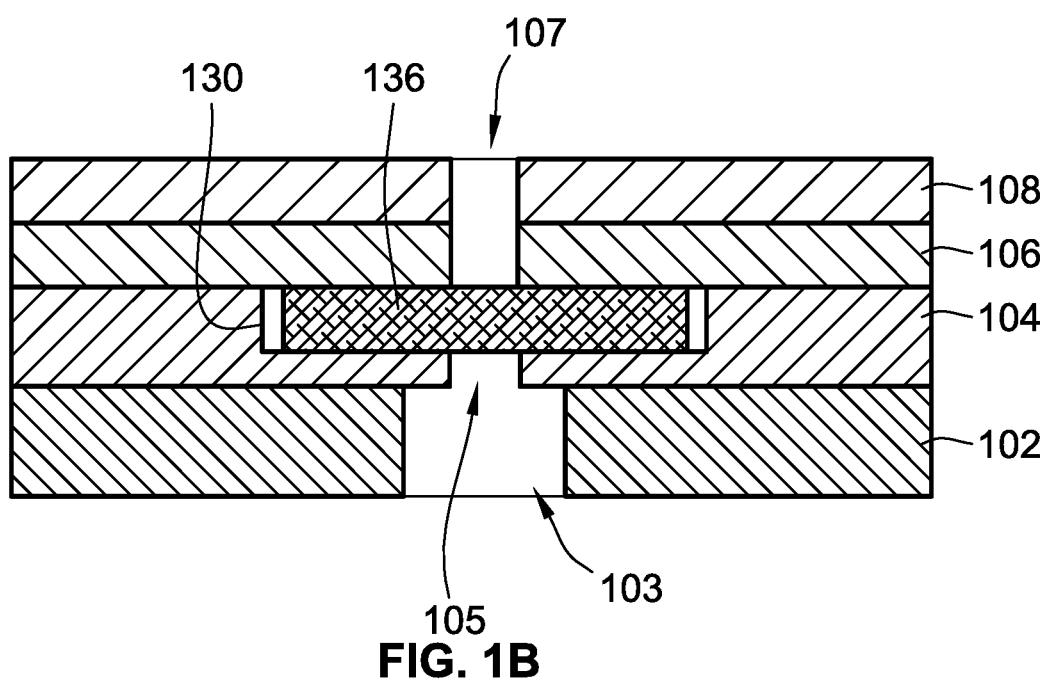
FIG. 1B shows a diagrammatic view of the stack-up of the layers of a sensor patch according to some embodiments of the invention.

FIG. 1B shows a cross-sectional view along the line 1B-1B in FIG. 1A according to some embodiments of the invention. The adhesive layer 102 can include one or more inlet ports 103 that align with inlet ports 105 in the bottom layer 104. The bottom layer 104 can be etched or embossed to include one or more sensing chambers 130 and the sensing chambers 130 can include colorimetric sensing substrate materials 132, 134, 136, 138, and 140 that change color or color intensity upon coming in contact with predefined components of perspiration, such as salts (e.g., sodium ions, chloride ions), glucose, and lactate, to name just a few examples. The top layer 106 can be bonded to the bottom layer 104 using an adhesive layer or by plasma bonding (e.g., plasma oxygen bonding). The NFC layer 108 can be bonded to the top layer 106 using an adhesive or plasma bonding. Both the top layer 106 and the NFC layer 108 can include holes for vent ports 107 to reduce the back pressure. The vent ports 107 can be etched or embossed into the layers 106, 108 to form channels that extend to the edges of the sensor patch 100.

The stack-up can be assembled using various methods. Each of the individual layers can be fabricated using a roll-to-roll or reel-to-reel fabrication process. For example, the adhesive layer 102 can be fabricated on a roll-to-roll web (e.g., n sensor patches across) and the outer margins and the inlet ports 103 can be die cut or laser cut to remove those sections from the web. Similarly, the bottom layer 104 and the layers 106, 108 can be fabricated on a roll-to-roll web (e.g., n sensor patches across) and the outer margins and the vent ports 107 can be die cut or laser cut to remove those sections from the web. The features (e.g., the perspiration volume sensing channel 120 and the sensing chambers 130) can be embossed, laser etched or micro-molded into the polymer layer on the web. Final assembly can include roll-to-roll transfer of each of the layers of the stack-up onto either the adhesive layer 102 or the top layer 106 or NFC layer 108. Where the final assembly stacks the layers on the adhesive layer 102, the color reference marks 152, 154 can be printed on the top layer 106 or the NFC layer 108 after assembly. Where the final assembly stacks the layers on the top layer 106 or NFC layer, the top layer 106 or NFC layer 108 can be pre-printed with the color reference marks 152, 154 prior to assembly.

Figure 2A:
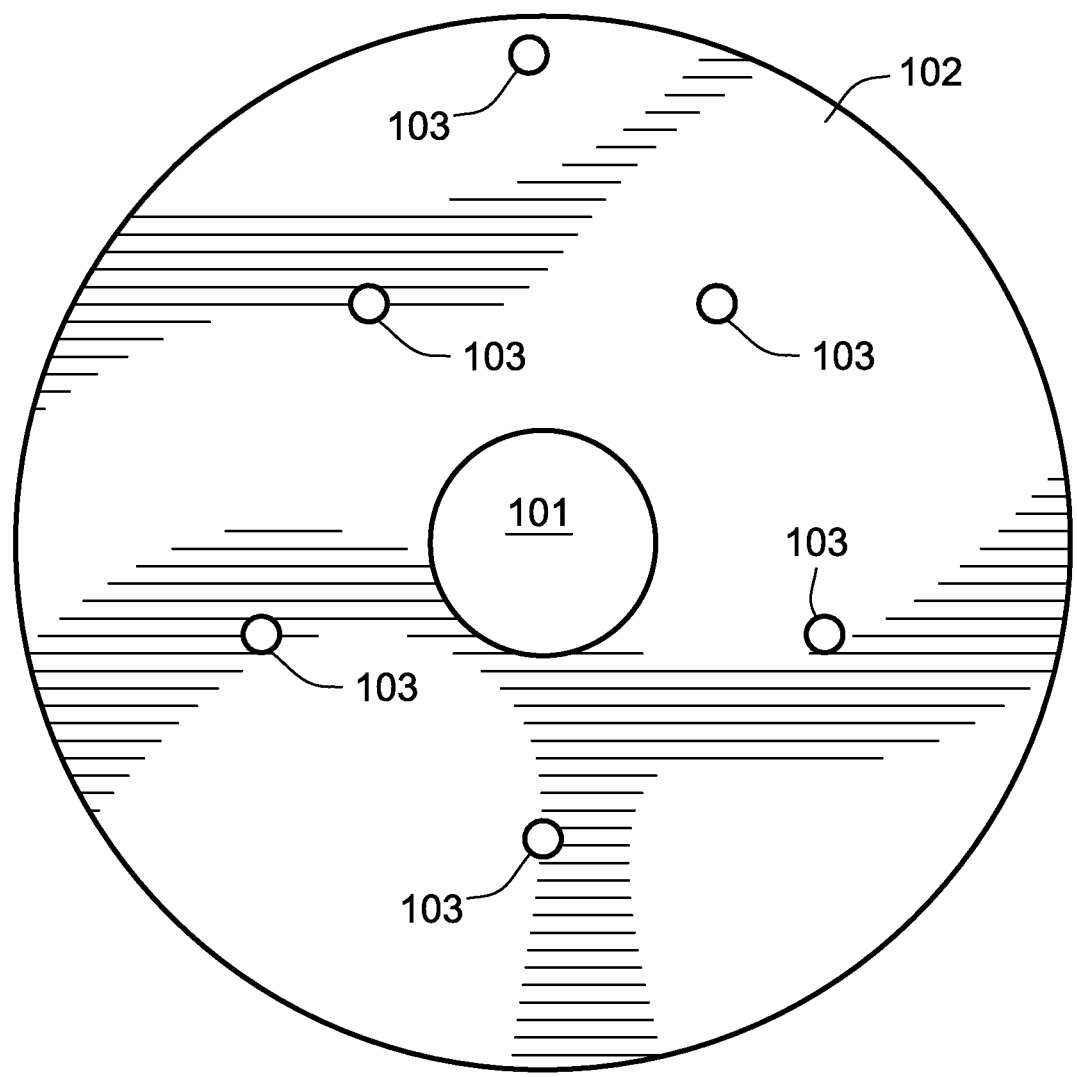
FIG. 2A shows a diagrammatic view of the adhesive layer according to some embodiments of the invention.

FIGS. 2A-2D show diagrammatic views of the individual layers that can be used to construct the sensor patch 100 according to some embodiments of the invention. FIG. 2A shows a diagrammatic view of an adhesive layer 102. The adhesive layer 102 aids in adhering the sensor patch 100 to a user, such as to the skin of a user. In some embodiments of the invention, the adhesive layer 102 can be considered a layer of the sensor patch 100. Alternatively, the adhesive layer 102 can be considered a separate and distinct layer from the sensor patch 100, such as when the sensor patch 100 does not come with an adhesive layer 102.

Figure 2B:
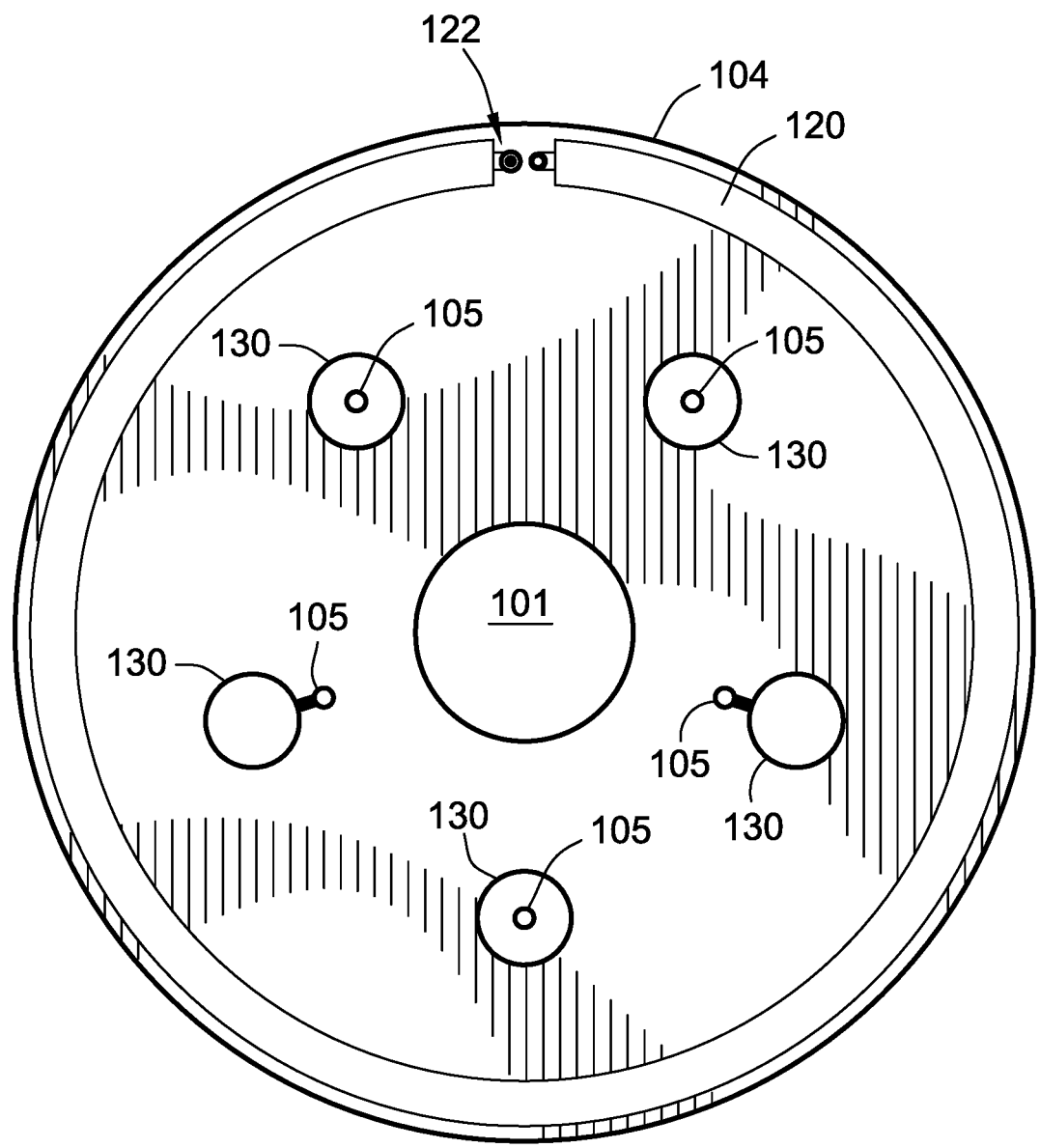
FIG. 2B shows a diagrammatic view of the bottom layer according to some embodiments of the invention.

The adhesive layer 102 can include a plurality of ports 103. The ports 103 allow perspiration to cross through the adhesive layer 102 and enter the sensor patch 100 or one or more additional layers of the sensor patch 100, discussed below. One or more of the ports 103 can align with the inlet port 122 discussed above. In addition, one or more of the ports 103 can align with other holes and/or ports discussed below (FIG. 2B). The ports 103 can be in the range from about 1 mm to about 5 mm in diameter depending on the desired volume of perspiration to be collected at the associated inlet port. In accordance with some embodiments, a single port 103 in the adhesive layer 102 can be open to all the ports within the above layers (such as the bottom layer 104 discussed below). In this configuration, motion of the un-adhered portion(s) of sensor patch 100 caused by physical activity can provide for pumping of perspiration into the inlet ports.

The adhesive layer 102 can be formed of any compatible adhesive material preferably strong enough to adhere the sensor patch 100 to the skin of the user when it is wet, dirty, and/or includes substantial amounts of hair. Examples of these adhesives include individual or combinations of adhesives selected from the group consisting of silicone gel adhesive, a silicone pressure sensitive adhesive, an acrylic pressure sensitive adhesive, a natural or synthetic rubber adhesive, and hydrocolloid adhesives. However, any type of pressure sensitive adhesive, permanent adhesive, and/or removable adhesive element, such as an adhesive tape, can be used.

The adhesive layer 102 can also include an absorbent, wicking, or hydrophilic material that captures perspiration as it enters the ports 103 and directs the captured perspiration toward the inlet ports. The absorbent, wicking, or hydrophilic material can include one or more of the following materials: porous absorbent paper, open-cell or closed-cell foam, woven or non-woven fabrics, microfiber cloth, and nano-fiber mesh.

FIG. 2B shows a diagrammatic view of the bottom layer 104 of the sensor patch 100. The description of the bottom layer 104 as the "bottom" layer is merely for convenience of explanation and is not meant to be limiting. For example, in some embodiments of the invention where the adhesive layer 102 is considered part of the sensor patch 100, the adhesive layer 102 can be considered the "bottom" layer and the bottom layer 104 as described herein can be one of the middle layers of the sensor patch 100.

The bottom layer 104 can include the features of the sensor patch 100 including one or more perspiration channels forming the perspiration volume sensing channel 120 and/or the one or more sensing chambers 130. The bottom layer 104 can also include the inlet ports 122 and/or one or more inlet ports 105 that enable perspiration to enter the perspiration volume sensing channel 120 and the sensing chambers 130, respectively.

The size of the inlet ports 122, 105 can be determined based on the desired operation of the sensor patch 100. For example, using the known pore density on the skin, the size of the inlet ports 122, 105 can be selected to expose a predefined number of sweat glands to each inlet port and then the size of perspiration volume sensing channel 120 and the sensing chambers 130 can be determined based on the sensitivity of colorimetric coatings, assays, and materials to achieve the desired performance. In accordance with some embodiments, the inlet ports 122, 105 can be in the range of about 0.25 mm to about 1 mm or more, depending on the desired amount of perspiration collection. Using the adhesive layer 102, the inlet ports 122, 105 are sealed to the skin enabling the sweat gland to pump perspiration into the inlet ports 122, 105 and then using pressure and capillary action, the perspiration flows into the perspiration volume sensing channel 120 and the sensing chambers 130. In accordance with some embodiments, hydrophilic, absorbent, and/or wicking materials can be included in the inlet ports 122, 105, the perspiration volume sensing channel 120, and the sensing chambers 130 to aide in the flow of perspiration to the desired locations within the sensor patch 100.

In accordance with some embodiments, the bottom layer 104 can be formed by combining two or more layers of material, one layer including the inlet ports 122, 105 and the other layer defining the features (e.g., the perspiration volume sensing channel 120 and sensing chambers 130). Alternatively, the inlet ports 122, 105 and the features can be laser micro-molded, die cut, etched, and/or embossed into the bottom layer. The bottom layer can be in the range from about 200 μm to about 700 μm in thickness and the features can be in the range from about 100 μm to about 500 μm deep into the bottom layer 104.

Figure 2C:
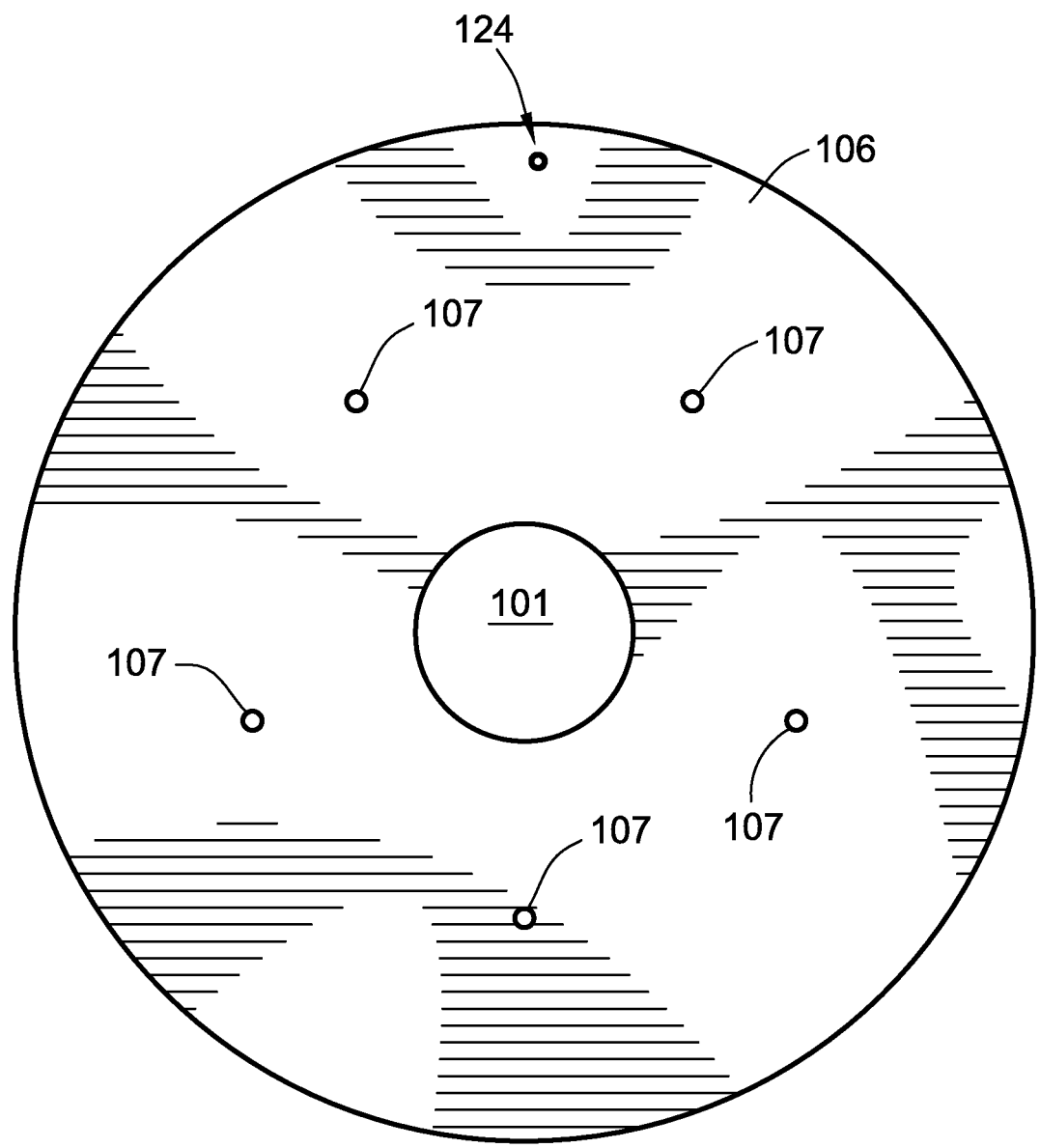
FIG. 2C shows a diagrammatic view of the top layer according to some embodiments of the invention.

FIG. 2C shows a diagrammatic view of the top layer 106 of the sensor patch 100. The description of the top layer 106 as the "top" layer is merely for convenience of explanation and is not meant to be limiting. For example, in some embodiments of the invention where the layer 108 (discussed below) is present on the sensor patch 100, the layer 106 can be considered the "top" layer and the top layer 106 as described herein can be one of the middle layers of the sensor patch 100.

FIG. 2C shows the top layer 106 which includes the vent ports 124, 107. The vent ports 124, 107 reduce the back pressure by connecting the perspiration volume sensing channel 120 and the sensing chambers 130 to the outside environment above the sensor patch and enable air to escape as the perspiration flows into the perspiration volume sensing channel 120 and the sensing chamber 130. The vent ports 124, 107 can be in the range from about 50 μm to about 250 μm in diameter depending on the desired perspiration flow. The top layer 106 can be in the range from about 100 μm to about 400 μm thick.

Figure 2D:
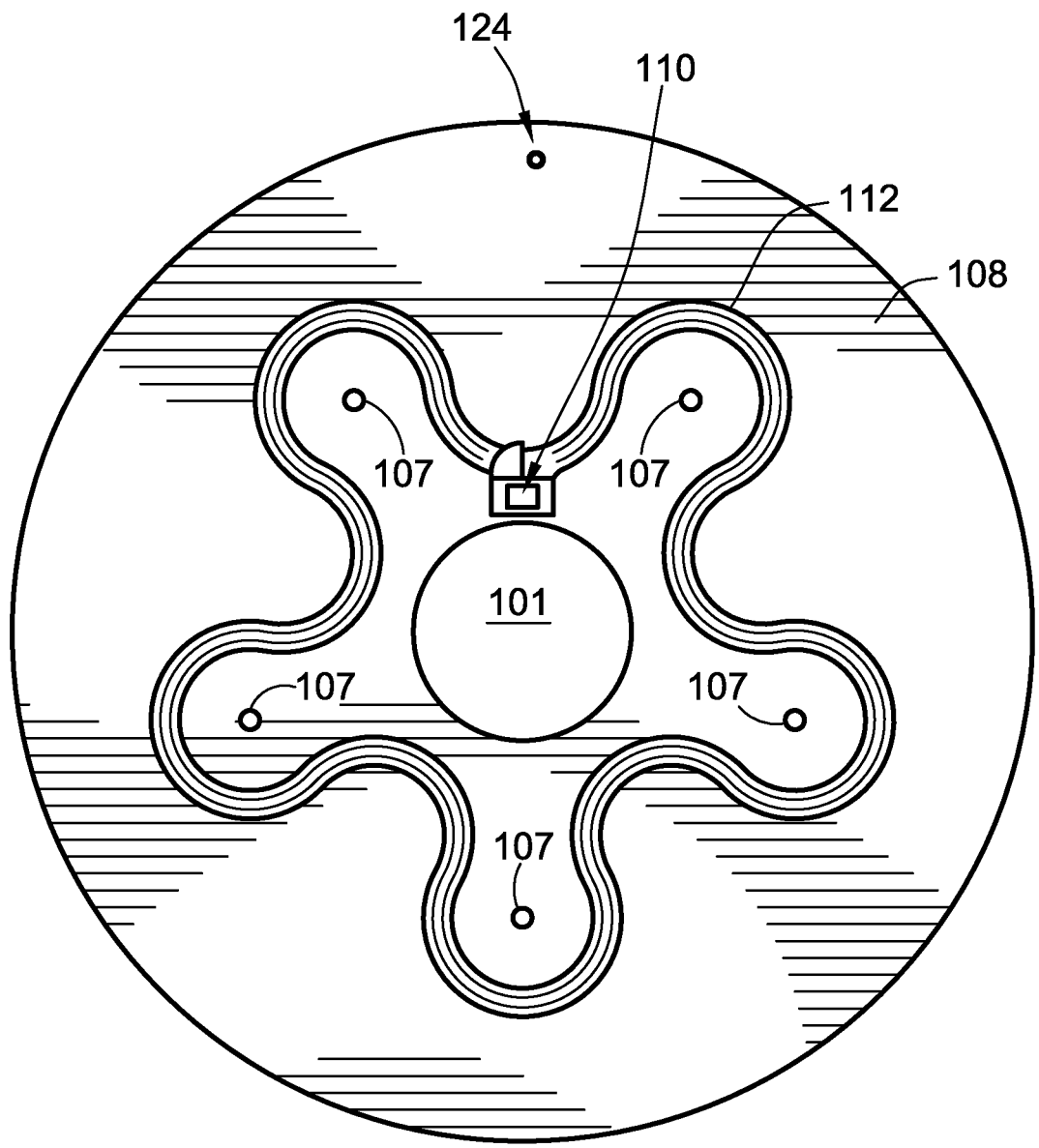
FIG. 2D shows a diagrammatic view of an alternative top layer according to some embodiments of the invention.

FIG. 2D shows an NFC layer 108, which is similar to the top layer 106 but includes the NFC chip 110 and the NFC antenna 112. In this embodiment, the NFC antenna 112 can be fabricated directly on a silicone elastomeric or polyimide substrate that can be die cut or laser etched to include the vent ports 124, 107. The NFC layer 108 can be in the range from about 100 μm to about 400 μm thick.

Figure 3:
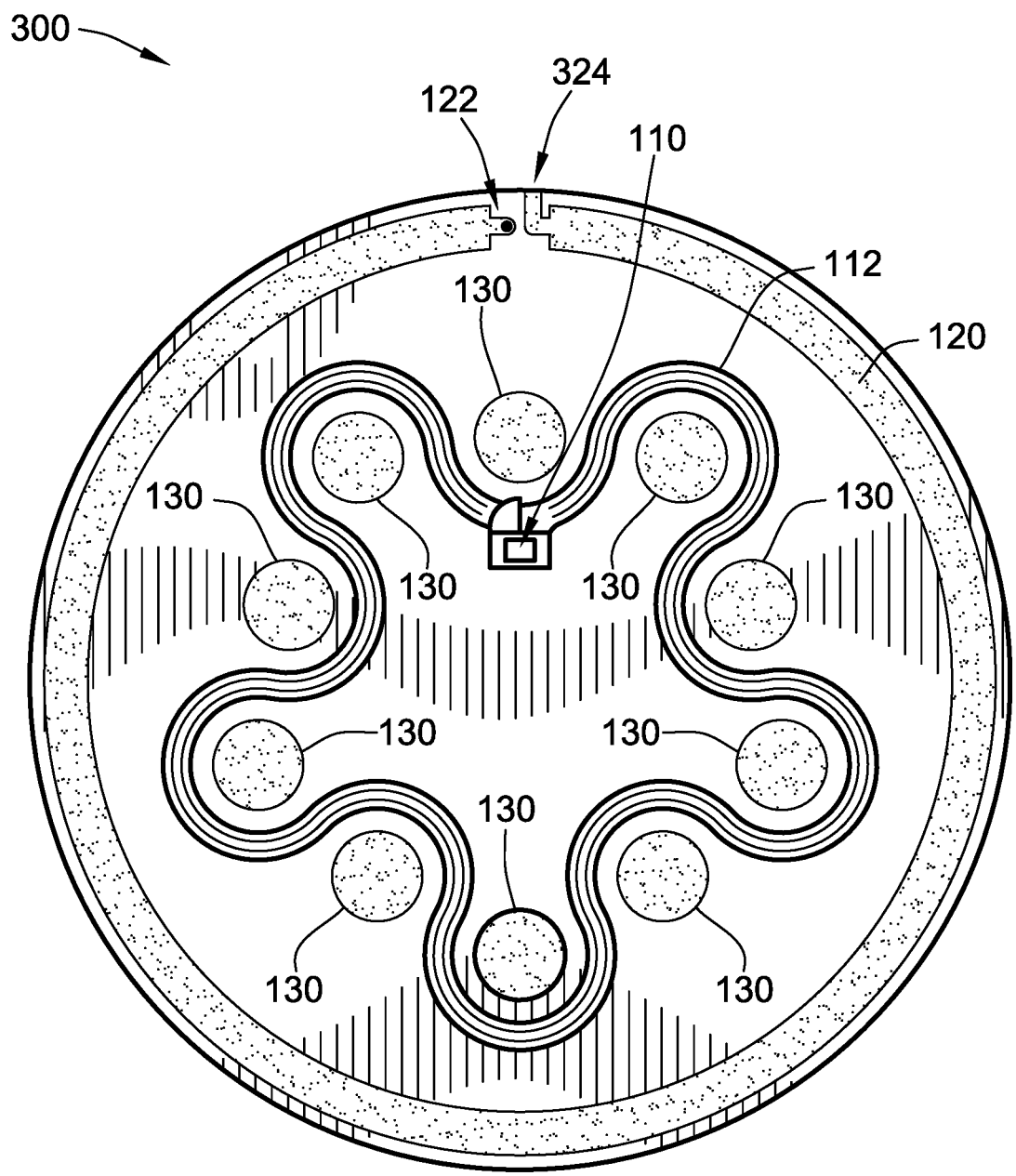
FIG. 3 shows a diagrammatic view of a sensor patch according to some embodiments of the invention.

FIG. 3 shows an alternative embodiment of a sensor patch 300 according to some embodiments of the invention. In this embodiment, more sensing chambers 130 are provided as compared to the sensor patch 100. Each of the sensing chambers 130 can include a different colorimetric assay or color changing material to enable the sensor patch 300 to detect many different components of perspiration. Alternatively, two or more of the sensing chambers 130 can be configured with the same colorimetric assay or color changing material to provide multiple sensors for quantifying a specific component of perspiration.

FIG. 3 also shows an alternative vent port 324 configuration. In this configuration, the vent port 324 extends out of the side edge of the sensor patch 300. The vent port 324 can be in the range from about 50 μm to about 250 μm in diameter depending on the desired perspiration flow. The port 324 can have other geometries, such as square, rectangular, etc., and have similar dimensions as the diameter discussed above, such as about 50 μm to about 250 μm in length, or arc length of the patch 300, or the like. In this embodiment, the vent port 324 can be laser etched or embossed into the bottom layer 104 and run to the outer edge of the layer. Where a feature might interfere with the run of the vent port 324 (such as a vent port running from a sensing chamber 130), a relatively large diameter hole (e.g., about 2 mm or more) can be cut or punched into the sensor patch 100. For example, vent ports extending from sensing chambers 130 can run to central hole 101 shown in FIG. 1.

The inlet ports 122 and the vent ports 324, 107 leading to each of the sensing chambers 130 can be different sizes to measure different rates. For example, sensing material inside a sensing chamber 130 having a large inlet port 103 port is likely to become saturated relatively quickly, where as an adjacent sensing chamber 130 having a smaller inlet port 105 is more likely to provide an accurate measure of a sensed component of perspiration over a longer period of time and a comparison of the two sensing chambers 130 can be used to detect changes in the component composition over time (e.g., the change in salt concentration as the user becomes dehydrated).

Figure 4:
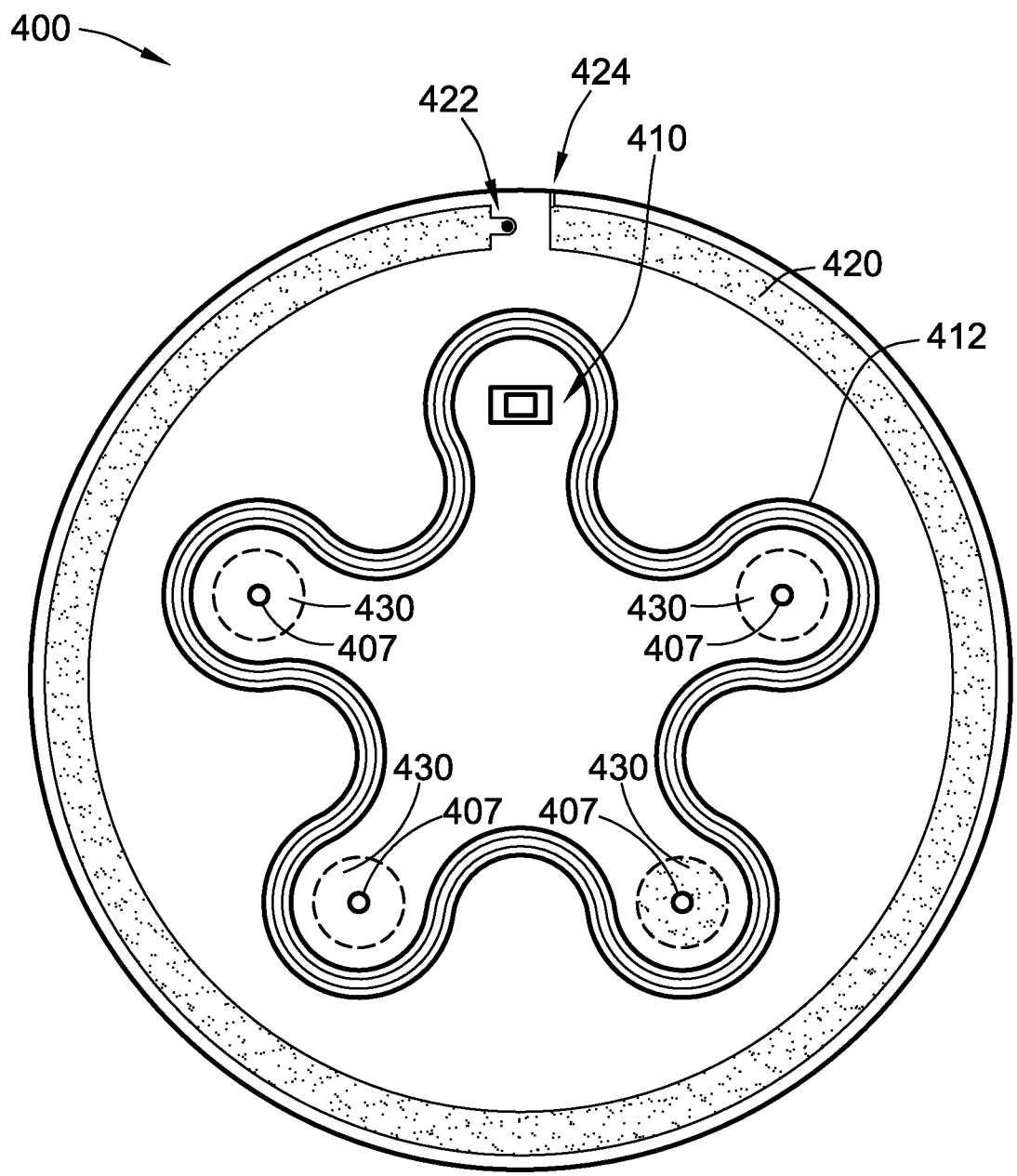
FIG. 4 shows a diagrammatic view of a sensor patch according to some embodiments of the invention.

FIG. 4 shows an alternative embodiment of a sensor patch 400 according to some embodiments of the invention. The sensor patch 400 can include a NFC integrated circuit chip 410 and an NFC antenna 412, a perspiration volume and rate sensing channel 420 and one or more sensing chambers 430 for detecting and quantifying biochemical components of perspiration and/or pH. A biocompatible adhesive layer can be used to adhere the sensor patch to the skin, although, the patch can be integrated into a layer of clothing to hold it in position without the need for adhesives. The central section of the sensor patch 400 can include an opening or hole (not shown) to reduce the amount of skin surface area being covered and allow perspiration to escape. The perspiration volume and rate sensing channel 420 can extend from inlet port 422 to vent port 424 around the periphery of the sensor patch 400. Each of the sensing chambers 430 can include an inlet port on the bottom (not shown) and a vent port 407 on the top. Reference marks and color reference marks can also be provided (not shown).

Figure 5:
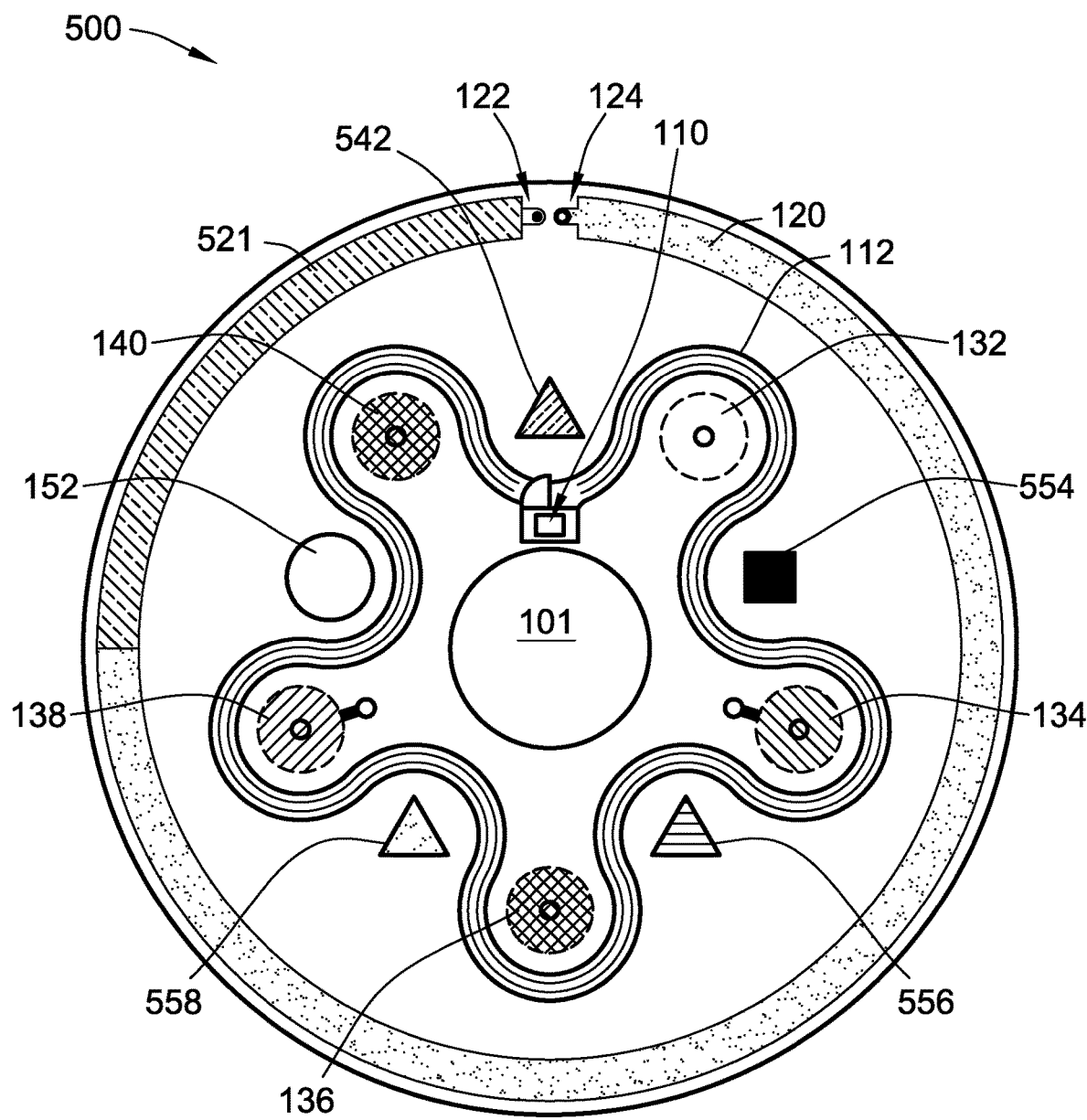
FIG. 5 shows a diagrammatic view of a sensor patch in use according to some embodiments of the invention.
Figure 6:
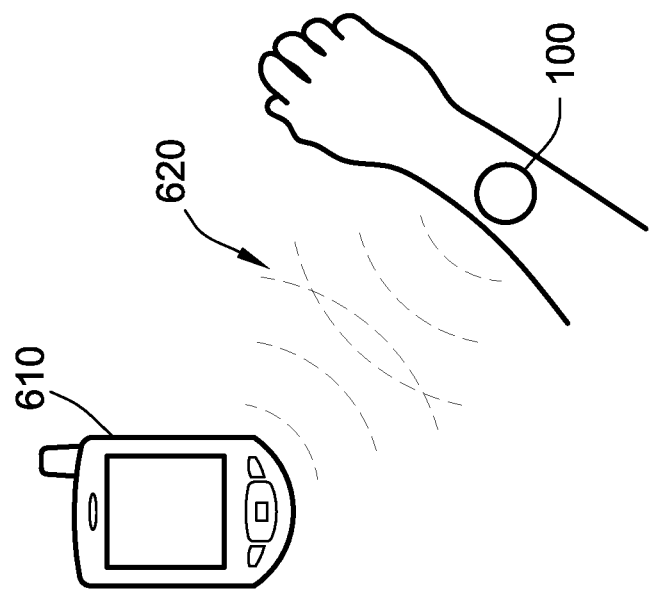
FIG. 6 shows a diagrammatic view of a system including a sensor patch and a smart device according to some embodiments of the invention.

Referring to FIG. 5, in operation, the user places the sensor patch 500 (or any patch disclosed herein) on a predefined location of the body, such as the arm, the leg or the abdomen. As the user begins to perspire, the perspiration will flow into the perspiration volume sensing channel 120 and begin to change the color of the perspiration sensitive coating or assay in the perspiration volume sensing channel 120 as shown in FIG. 6 as shown by the hatched portion 521. In addition, perspiration will flow into the sensing chambers 130 and components of the perspiration will react with the colorimetric assays and materials 132, 134, 136, 138, and 140 in the sensing chambers resulting in a color change of the sensing chambers 130, as shown in FIG. 6. The sensor patch 500 can include printed indicia in the form of registration and color reference marks 152, 542, 554, 556, 558 on the top surface (e.g., the top layer 106 or 108) of the sensor patch 500 that are printed in predefined locations and provide location reference marks and/or color calibration reference marks.

As shown in FIG. 6, the user can place their smart device 610 (or other sensing device) near the sensor patch 100 on their body and the NFC chip 110 and NFC antenna 112 of the sensor patch 100 will communicate (as represented by the waves 620) with the smart device 610 and cause the smart device 610 to load and execute an application that can perform various functions. In accordance with some embodiments, the smart device 610 can load an application that assists the user with acquiring an image (e.g., a photograph or a video) of the sensor patch 100 on his or her body. The application can guide the user to use the camera in the smart device 610 to acquire the image by providing guide marks on the smart device 610 screen to position the sensor patch 100 in the image. The application of the smart device 610 or a remote application (e.g., a cloud based application) can analyze the image of the sensor patch 100 to identify the location reference marks and the color calibration reference marks, e.g., as shown in FIGS. 1 and 5. The registration marks and/or color reference marks 152, 154 can be used to locate each of the sensing chambers 130. The application can use the color reference marks 152, 154 to calibrate the image for white balance and color intensity for the ambient light and then analyze the calibrated image to determine quantitatively the components of the user's perspiration. The image can also be analyzed to determine the volume and rate of perspiration using the perspiration volume sensing channel 120 by determining the portion that has changed color as compared to the overall length of the perspiration volume sensing channel 120.

In accordance with some embodiments, the NFC chip 110 can include or be connected to a circuit that includes a heating element that can be controlled (e.g., turned on or off, or up or down) through interaction with the NFC chip 110 (e.g., loading a value in a register or memory location). The heating element can provide for local heating in order to induce perspiration with physical activity. Alternatively, the sensor patch 100 can include a battery or other power source to power the heating element without the need to keep the NFC reading device in close proximity.

In accordance with some embodiments, the NFC chip 110 can include or be connected to a thermistor or other temperature sensor that can be read using NFC communications (e.g., waves 620). The NFC chip can include or be connected to an analog to digital converter that converts the temperature sensor value to a digital value that can be converted to temperature. The temperature sensor can be placed close to the skin to provide a measure of skin surface temperature or insulated from the skin to provide a measure of ambient environmental temperatures. Skin temperature can be used to determine core body temperature as well as to determine vapor pressure and evaporation rates of perspiration and provide warnings to the user about unsafe conditions. The temperature sensor can also be positioned in or near the sensing chambers 130 to provide an indication of the temperature of the colorimetric assays used in the biochemical analysis of perspiration, to determine whether a threshold has been crossed indicating that the assay is no longer usable.

Figure 7:
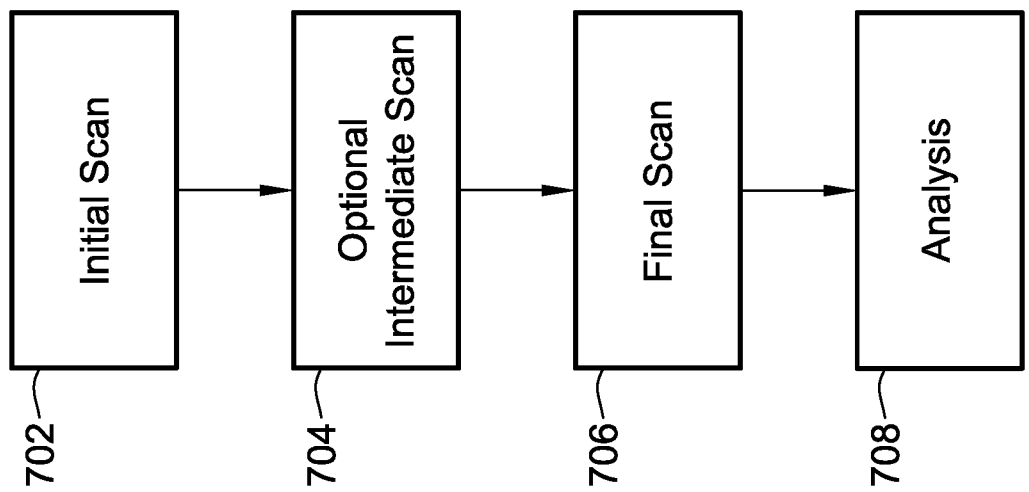
FIG. 7 shows a diagrammatic view of a method of using a sensor patch according to some embodiments of the invention.

FIG. 7 shows a flowchart of a method of using the sensor patch 100 with a smart device 610, such as a smart phone according to some embodiments of the invention. After the user places the sensor patch 100 on his or her body and before the user begins the activity that will induce perspiring (e.g., exercise or other physical activity), the user takes an initial scan (box 802) of the sensor patch 100, which results in an initial image of the sensor patch 100 prior to detecting perspiration. Each scan event can include the user placing the smart device 610 near the sensor patch 100 resulting in the NFC activation (e.g., waves 620) of the sensor patch 100 by smart device 610 as the reader and causing the NFC chip 110 in the sensor patch 100 to execute a function or task. The function can, for example, include the NFC chip 110 sending data (e.g., waves 620) to the smart device 610, which causes the performance of an operation or the execution of a program. The program can, for example, include providing an image with guidelines on the display that helps the user position the sensor patch 100 in an appropriate position to generate one or more images (e.g., by photograph or video). The flash can be used to reduce the impact of ambient lighting and shadows. This image can be compared to later images of the sensor patch 100 to determine the amount and rate of perspiration as well as the component elements of perspiration. After the user begins to perspire, the user or another person can optionally take intermediate scans of the sensor patch 100 during the activity to determine intermediate perspiration readings (box 704). After the user has completed the physical activity, the user can take a final scan (box 706) of the sensor patch 100 using the smart device 610. In addition to recording the image of the sensor patch 100, the smart device 610 can also record other information, such as time and date; environmental temperature, humidity, and/or pressure; and location, including elevation (e.g., using GPS coordinates) for each image. This information can be stored and used to adjust the perspiration data, as well as for other determinations. An application in the smart device 610 can compare and analyze the images to determine the perspiration volume, rates, and/or component information or the application can forward the images to a remote computer (e.g., a cloud based application) to analyze the images and determine the perspiration volume, rates, and/or component information.

The analysis can include using the location reference marks to orient and scale the images of the sensor patch 100 such that the locations of the perspiration volume sensing channel 120 and locations of the individual sensing chambers 130 can be identified in each image. Next, the analysis can include calibrating the color and brightness of the image to accommodate a broad range of ambient light conditions and different camera color calibrations using the color calibration reference marks. The calibrated images can be used to determine the perspiration volume and component information.

From the perspiration volume sensing channel 120, the length of the color change can be correlated to a volume of perspiration as function of the known volume of the perspiration volume sensing channel 120 (e.g., the cross-sectional area times the length of the color change area) provides a measure of the perspiration volume. The perspiration rate can be determined by time between scans, which can be calculated from the date and time stamps of the images (e.g., from the operating system or the meta-data of the images).

For the sensing chambers 130, the location of each chamber can be determined in the calibrated image and a color value (e.g., in RGB or color value, hue, and saturation) can be determined for each location of each sensing chamber 130. Based on the known location, the color value can be compared to a reference table that provides a quantitative indication of the detected component of perspiration for that sensing chamber 130. Depending on the assay or the color sensitivity of the assay material 132, 134, 136, 138, and 140 in the sensing chambers 130, the color itself, the color brightness or hue (and optionally, the length of time) can be used to determine a quantitative measure of the biochemical element or pH detected in the user's perspiration. In accordance with some embodiments, the color indicator of the sensing chamber 130 can be further calibrated by subtracting or comparing the color of the sensing chamber from the initial scan to the color from the final scan.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:

1. A sensor patch comprising:
   a perspiration volume sensing channel including at least a first colorimetric material that changes color in response to exposure to perspiration;
   a perspiration component sensing chamber including at least a second colorimetric material that changes color in response to exposure to a biochemical component in the perspiration;
   a near field communication circuit and a near field communication antenna; and
   a plurality of the perspiration component sensing chamber, each perspiration component sensing chamber including a chamber inlet port in fluid communication with the perspiration component sensing chamber to allow the perspiration to enter into the perspiration component sensing chamber, wherein two or more of the plurality of chamber inlet ports have different diameters to measure different collection rates of the perspiration.

2. The sensor patch of claim 1, further comprising: a channel inlet port in fluid communication with the perspiration volume sensing channel to allow the perspiration to enter into the perspiration volume sensing channel.

3. The sensor patch of claim 2, further comprising:
a channel vent port in fluid communication with the perspiration volume sensing channel to reduce backpressure as the perspiration fills the perspiration volume sensing channel; and
a chamber vent port in fluid communication with the perspiration component sensing chamber to reduce backpressure as the perspiration fills the perspiration component sensing chamber.

4. The sensor patch of claim 3, wherein the channel vent port vents out of a surface of the sensor patch opposite from the channel inlet port.

5. The sensor patch of claim 3, wherein the channel vent port vents to an outer edge of the sensor patch perpendicular to the channel inlet port.

6. The sensor patch of claim 1, further comprising:
at least one indicia configured to have a shape, a size, a color, a location, or a combination thereof for calibrating an image of the sensor patch taken by a smart device.

7. The sensor patch of claim 1, further comprising:
an adhesive layer configured to attach the sensor patch to a surface of a user.

8. The sensor patch of claim 7, further comprising an integrated circuit that includes the near field communication circuit.

9. The sensor patch of claim 1, wherein each perspiration component sensing chamber includes a chamber vent port in fluid communication with the perspiration component sensing chamber and directly in fluid communication with an environment of the sensor patch to reduce backpressure as the perspiration fills the perspiration component sensing chamber.

10. The sensor patch of claim 9, wherein the chamber inlet port is horizontally aligned with a corresponding chamber vent port and vertical axes defined by the chamber inlet port and the corresponding chamber vent port pass through a corresponding perspiration component sensing chamber for at least one of the plurality of the perspiration component sensing chamber.

11. The sensor patch of claim 9, further comprising:
a channel inlet port in fluid communication with the perspiration volume sensing channel to allow the perspiration to enter into the perspiration volume sensing channel; and
a channel vent port in fluid communication with the perspiration volume sensing channel to reduce backpressure as the perspiration fills the perspiration volume sensing channel,
wherein the sensor patch has a bottom surface and a top surface opposite the bottom surface, and wherein the channel inlet port and the plurality of chamber inlet ports are on the bottom surface and the channel vent port and the plurality of chamber vent ports are on the top surface.

12. A method of using a smart device and a sensor patch placed on a surface of a user to determine one or more properties of perspiration from the user, the method comprising:
causing the smart device to interrogate a near field communication circuit of the sensor patch;
executing a function on the smart device to obtain at least one image of the sensor patch based on data sent from the near field communication circuit in response to the interrogation;
analyzing the at least one image to determine a volume of the perspiration, a rate of the perspiration, one or more components within the perspiration, or a combination thereof and determining a first length of a color change within a perspiration channel of the sensor patch;
comparing the first length of the color change with a second length of the color change within the perspiration channel of the sensor patch from analysis of at least one other image of the sensor patch; and
determining the rate of the perspiration based on the comparison of the first length to the second length.

13. The method of claim 12, further comprising:
calibrating the at least one image based on one or more indicia visible on the sensor patch and captured in the at least one image.

14. The method of claim 13, wherein the calibration includes orienting and scaling the at least one image, adjusting a white balance of the at least one image based on a color of the one or more indicia, or a combination thereof.

15. The method of claim 12, wherein the analysis comprises determining a quantitative measure of one or more elements in the perspiration based on a color hue, a color value, a color intensity, or a combination thereof of a colorimetric material within a sensing chamber of the sensor patch.

16. The method of claim 12, further comprising:
determining an amount of time between acquisition of the at least one image and the at least one other image based, at least in part, on date stamps, time stamps, or a combination thereof of the at least one image and the at least one other image,
wherein the determination of the rate is based on the amount of time.

17. The method of claim 12, wherein the analysis comprises determining the volume of the perspiration based on a volume of the perspiration channel and the first length of the color change.

18. The method of claim 12, further comprising:
determining, by the smart device, a temperature, a humidity, a pressure, a location, an elevation, or a combination thereof of an environment of the sensor patch as metadata; and
tagging the at least one image with the metadata for use in the analysis of the at least one image.

19. A method of using a smart device and a sensor patch placed on a surface of a user to determine one or more properties of perspiration from the user, the method comprising:
causing the smart device to interrogate a near field communication circuit of the sensor patch;
executing a function on the smart device to obtain at least one image of the sensor patch based on data sent from the near field communication circuit in response to the interrogation; and
analyzing the at least one image to determine a volume of the perspiration, a rate of the perspiration, one or more components within the perspiration, or a combination thereof, wherein the analysis comprises determining a first length of a color change within a perspiration channel of the sensor patch and determining the volume of perspiration based on a volume of the perspiration channel and the first length of the color change.

20. The method of claim 19, further comprising:
calibrating the at least one image based on one or more indicia visible on the sensor patch and captured in the at least one image.

21. The method of claim 20, wherein the calibration includes orienting and scaling the at least one image, adjusting a white balance of the at least one image based on a color of the one or more indicia, or a combination thereof.

22. The method of claim 19, wherein the analysis comprises determining a quantitative measure of one or more elements in the perspiration based on a color hue, a color value, a color intensity, or a combination thereof of a colorimetric material within a sensing chamber of the sensor patch.

23. The method of claim 19, further comprising: comparing the first length of the color change with a second length of the color change within the perspiration channel of the sensor patch from analysis of at least one other image of the sensor patch; determining the rate of the perspiration based on the comparison of the first length to the second length; and determining an amount of time between acquisition of the at least one image and the at least one other image based, at least in part, on date stamps, time stamps, or a combination thereof of the at least one image and the at least one other image, wherein the determination of the rate is based on the amount of time.

24. The method of claim 19, further comprising:
determining, by the smart device, a temperature, a humidity, a pressure, a location, an elevation, or a combination thereof as metadata; and
tagging the at least one image with the metadata for use in the analysis of the at least one image.

* * * * *